US012758652B2

(12) United States Patent
Lek et al.

(10) Patent No.: US 12,758,652 B2
(45) Date of Patent: Oct. 13, 2026

(54) COMPOSITIONS AND METHODS FOR UPREGULATING ISOFORMS OF DYSTROPHIN AS THERAPY FOR DUCHENNE MUSCULAR DYSTROPHY (DMD)

(71) Applicant: YALE UNIVERSITY, New Haven, CT (US)

(72) Inventors: Monkol Lek, North Haven, CT (US); Angela Lek, North Haven, CT (US); Keryn Woodman, New Haven, CT (US); Kaiyue Ma, New Haven, CT (US)

(73) Assignee: Yale University, New Haven, CT (US)

( * ) Notice: Subject to any disclaimer, the term of this patent is extended or adjusted under 35 U.S.C. 154(b) by 1114 days.

(21) Appl. No.: 17/767,852

(22) PCT Filed: Oct. 9, 2020

(86) PCT No.: PCT/US2020/055089
§ 371 (c)(1),
(2) Date: Apr. 8, 2022

(87) PCT Pub. No.: WO2021/072276
PCT Pub. Date: Apr. 15, 2021

(65) Prior Publication Data

US 2024/0091379 A1 Mar. 21, 2024

Related U.S. Application Data

(60) Provisional application No. 63/064,077, filed on Aug. 11, 2020, provisional application No. 62/913,935, filed on Oct. 11, 2019.

(51) Int. Cl.

| | |
|---|---|
| ***A61K 48/00*** | (2006.01) |
| ***A61P 21/00*** | (2006.01) |
| ***C12N 9/22*** | (2006.01) |
| ***C12N 15/113*** | (2010.01) |
| ***C12N 15/86*** | (2006.01) |

(52) U.S. Cl.
CPC ............ *A61K 48/005* (2013.01); *A61P 21/00* (2018.01); *C12N 9/22* (2013.01); *C12N 15/113* (2013.01); *C12N 15/86* (2013.01); *C12N 2310/20* (2017.05); *C12N 2750/14143* (2013.01)

(58) Field of Classification Search
CPC ......... A61K 48/005; A61P 21/00; C12N 9/22; C12N 15/113; C12N 15/86; C12N 2310/20; C12N 2750/14143; C12N 2320/34; C12N 2330/51
See application file for complete search history.

(56) References Cited

U.S. PATENT DOCUMENTS

| | | | |
|---|---|---|---|
| 2018/0258429 A1 | 9/2018 | Saetrom et al. | |
| 2018/0265859 A1 | 9/2018 | Tremblay et al. | |
| 2018/0353615 A1 | 12/2018 | Gersbach et al. | |

FOREIGN PATENT DOCUMENTS

| | | | |
|---|---|---|---|
| WO | 2018129296 A1 | 7/2018 | |
| WO | WO-2018128689 A1 * | 7/2018 | ........... A61K 31/195 |

OTHER PUBLICATIONS

Hugnot, Jean-Philippe, et al. "Striking Conservation of the Brain-Specific Region of the Dystrophin Gene." Mammalian Genome, vol. 4, No. 7, 1993, pp. 393-396. DOI.org (Crossref), https://doi.org/10.1007/BF00360592. (Year: 1993).*
Cox, Gregory A., et al. "Dp71 Can Restore the Dystrophin-Associated Glycoprotein Complex in Muscle but Fails to Prevent Dystrophy." Nature Genetics, vol. 8, No. 4, Dec. 1994, pp. 333-339. DOI.org (Crossref), https://doi.org/10.1038/ng1294-333. (Year: 1994).*
Bastianutto, C. "Dystrophin Muscle Enhancer 1 Is Implicated in the Activation of Non-Muscle Isoforms in the Skeletal Muscle of Patients with X-Linked Dilated Cardiomyopathy." Human Molecular Genetics, vol. 10, No. 23, Nov. 2001, pp. 2627-2635. DOI.org (Crossref), https://doi.org/10.1093/hmg/10.23.2627. (Year: 2001).*
Bastianutto, Carlo, et al. "A Novel Muscle-Specific Enhancer Identified within the Deletion Overlap Region of Two XLDC Patients Lacking Muscle Exon 1 of the Human Dystrophin Gene." Genomics, vol. 80, No. 6, Dec. 2002, pp. 614-620. DOI.org (Crossref), https://doi.org/10.1006/geno.2002.7015. (Year: 2002).*
Leiden: Dystrophin Isoforms and Their Expression. Last modified Mar. 5, 2006. https://www.dmd.nl/isoforms.html. Accessed Apr. 15, 2025. (Year: 2006).*
Salva, Maja Z., et al. "Design of Tissue-Specific Regulatory Cassettes for High-Level rAAV-Mediated Expression in Skeletal and Cardiac Muscle." Molecular Therapy, vol. 15, No. 2, Feb. 2007, pp. 320-329. DOI.org (Crossref), https://doi.org/10.1038/sj.mt.6300027. (Year: 2007).*
Barrangou, Rodolphe, and Jennifer A. Doudna. "Applications of CRISPR Technologies in Research and Beyond." Nature Biotechnology, vol. 34, No. 9, Sep. 2016, pp. 933-941. DOI.org (Crossref), https://doi.org/10.1038/nbt.3659. (Year: 2016).*
Doorenweerd, Nathalie, et al. "Timing and Localization of Human Dystrophin Isoform Expression Provide Insights into the Cognitive Phenotype of Duchenne Muscular Dystrophy." Scientific Reports, vol. 7, No. 1, Oct. 2017, p. 12575. DOI.org (Crossref), https://doi.org/10.1038/s41598-017-12981-5. (Year: 2017).*
Kemaladewi, Dwi U., et al. "A Mutation-Independent Approach for Muscular Dystrophy via Upregulation of a Modifier Gene." Nature, vol. 572, No. 7767, Aug. 2019, pp. 125-130. DOI.org (Crossref), https://doi.org/10.1038/s41586-019-1430-x. (Year: 2019).*

(Continued)

*Primary Examiner* — J. E. Angell
*Assistant Examiner* — Sarah E Allen
(74) *Attorney, Agent, or Firm* — Saul Ewing LLP; Justin Crotty; Kathryn Doyle

(57) ABSTRACT

The present invention includes methods for treating a disease or disorder that is associated with aberrant or absent dystrophin, by upregulating a brain isoform of dystrophin (e.g. purkinje and/or cortical) in a subject in need thereof.

5 Claims, 8 Drawing Sheets

Specification includes a Sequence Listing.

(56) References Cited

OTHER PUBLICATIONS

Martella, Andrea, et al. "Systematic Evaluation of CRISPRa and CRISPRi Modalities Enables Development of a Multiplexed, Orthogonal Gene Activation and Repression System." ACS Synthetic Biology, vol. 8, No. 9, Sep. 2019, pp. 1998-2006. DOI.org (Crossref), https://doi.org/10.1021/acssynbio.8b00527. (Year: 2019).*
Min, Yi-Li, et al. "CRISPR Correction of Duchenne Muscular Dystrophy." Annual Review of Medicine, vol. 70, No. 1, Jan. 2019, pp. 239-255. DOI.org (Crossref), https://doi.org/10.1146/annurev-med-081117-010451. (Year: 2019).*
Ramos, Julian N., et al. "Development of Novel Micro-Dystrophins with Enhanced Functionality." Molecular Therapy, vol. 27, No. 3, Mar. 2019, pp. 623-635. DOI.org (Crossref), https://doi.org/10.1016/j.ymthe.2019.01.002. (Year: 2019).*
Becirovic, Elvir. "Maybe You Can Turn Me on: CRISPRa-Based Strategies for Therapeutic Applications." Cellular and Molecular Life Sciences, vol. 79, No. 2, Feb. 2022, p. 130. DOI.org (Crossref), https://doi.org/10.1007/s00018-022-04175-8. (Year: 2022).*
Matharu, Navneet, et al. "CRISPR-Mediated Activation of a Promoter or Enhancer Rescues Obesity Caused by Haploinsufficiency." Science, vol. 363, No. 6424, Jan. 2019, p. eaau0629. (Year: 2019).*
International Search Report and Written Opinion issued on Feb. 8, 2021, for International Application No. PCT/US2020/055089.
Nakamura "X-linked dilated cardiomyopathy: a cardiospecific phenotype of dystrophinopathy." Pharmaceuticals 8.2 (2015): 303-320.

* cited by examiner

FIG. 6
AAV Treated hDMD mdx D2 Hearts
4 Week High Dose
8 Week High Dose
Control
8341
3005
3006
3007
3008
Control
8384
3009
3010
3011
3012
SaCas9
Vinculin

SEQUENCE LISTING

```
<160> NUMBER OF SEQ ID NOS: 13

<210> SEQ ID NO 1
<211> LENGTH: 22
<212> TYPE: DNA
<213> ORGANISM: Artificial Sequence
<220> FEATURE:
<223> OTHER INFORMATION: gRNA

<400> SEQUENCE: 1

gagtgagtga tcccaacact ga                                              22


<210> SEQ ID NO 2
<211> LENGTH: 22
<212> TYPE: DNA
<213> ORGANISM: Artificial Sequence
<220> FEATURE:
<223> OTHER INFORMATION: gRNA

<400> SEQUENCE: 2
```

gtgaaatatc cgggggcctc ta 22

<210> SEQ ID NO 3
<211> LENGTH: 22
<212> TYPE: DNA
<213> ORGANISM: Artificial Sequence
<220> FEATURE:
<223> OTHER INFORMATION: gRNA

<400> SEQUENCE: 3
gcacttgctt gtgcgcaggt cc 22

<210> SEQ ID NO 4
<211> LENGTH: 21
<212> TYPE: DNA
<213> ORGANISM: Artificial Sequence
<220> FEATURE:
<223> OTHER INFORMATION: gRNA

<400> SEQUENCE: 4
gctttgcatc tgtacagaag a 21

<210> SEQ ID NO 5
<211> LENGTH: 22
<212> TYPE: DNA
<213> ORGANISM: Artificial Sequence
<220> FEATURE:
<223> OTHER INFORMATION: gRNA

<400> SEQUENCE: 5
gtcgactgac gtatcagata gt 22

<210> SEQ ID NO 6
<211> LENGTH: 22
<212> TYPE: DNA
<213> ORGANISM: Artificial Sequence
<220> FEATURE:
<223> OTHER INFORMATION: gRNA

<400> SEQUENCE: 6
gatcatgcga aaggggagct gt 22

<210> SEQ ID NO 7
<211> LENGTH: 21
<212> TYPE: DNA
<213> ORGANISM: Artificial Sequence
<220> FEATURE:
<223> OTHER INFORMATION: gRNA

<400> SEQUENCE: 7
ggcatgccca cctaacctaa c 21

<210> SEQ ID NO 8
<211> LENGTH: 22
<212> TYPE: DNA
<213> ORGANISM: Artificial Sequence
<220> FEATURE:
<223> OTHER INFORMATION: gRNA

<400> SEQUENCE: 8
gcacctcact attcacggca ac 22

<210> SEQ ID NO 9
<211> LENGTH: 22
<212> TYPE: DNA
<213> ORGANISM: Artificial Sequence
<220> FEATURE:
<223> OTHER INFORMATION: gRNA

<400> SEQUENCE: 9
gaagaaacca ttgctgtgag ag 22

<210> SEQ ID NO 10
<211> LENGTH: 22
<212> TYPE: DNA
<213> ORGANISM: Artificial Sequence
<220> FEATURE:
<223> OTHER INFORMATION: gRNA

<400> SEQUENCE: 10
gaactgtgtc gtctgcttta ta 22

<210> SEQ ID NO 11
<211> LENGTH: 7434
<212> TYPE: DNA
<213> ORGANISM: Artificial Sequence
<220> FEATURE:
<223> OTHER INFORMATION: Vector Double VP64 C7 guide

<400> SEQUENCE: 11
cctggtatct ttatagtcct gtcgggtttc gccacctctg acttgagcgt cgatttttgt 60
gatgctcgtc aggggggcgg agcctatgga aaaacgccag caacgcggcc tttttacggt 120
tcctggcctt ttgctggcct tttgctcaca tgtcctgcag gcagctgcgc gctcgctcgc 180
tcactgaggc cgcccgggcg tcgggcgacc tttggtcgcc cggcctcagt gagcgagcga 240
gcgcgcagag agggagtggc caactccatc actaggggtt cctgcggcct ctagactcga 300
gtgcccatgt aaggaggcaa ggcctgggga cacccgagat gcctggttat aattaaccca 360
gacatgtggc tgcccccccc cccccaacac ctgctgcctc taaaaataac cctgcatgcc 420
atgttcccgg cgaagggcca gctgtccccc gccagctaga ctcagcactt agtttaggaa 480
ccagtgagca agtcagccct tggggcagcc catacaaggc catggggctg ggcaagctgc 540
acgcctgggt ccggggtggg cacggtgccc gggcaacgag ctgaaagctc atctgctctc 600
aggggcccct ccctggggac agcccctcct ggctagtcac accctgtagg ctcctctata 660
taacccaggg gcacaggggc tgccctcatt ctaccaccac ctccacagca cagacagaca 720
ctcaggagcc agccagcacc ggtgccacca tgggtccgcg ggctgacgca ttggacgatt 780
ttgatctgga tatgctggga agtgacgccc tcgatgattt tgaccttgac atgcttggtt 840
cggatgccct tgatgacttt gacctcgaca tgctcggcag tgacgccctt gatgatttcg 900
acctggacat ggttaaccca aagaagaagc ggaaggtcgg tatccacgga gtcccagcag 960
ccaagcggaa ctacatcctg ggcctggcca tcggcatcac cagcgtgggc tacggcatca 1020
tcgactacga gacacgggac gtgatcgatg ccggcgtgcg gctgttcaaa gaggccaacg 1080
tggaaaacaa cgagggcagg cggagcaaga gaggcgccag aaggctgaag cggcggaggc 1140
ggcatagaat ccagagagtg aagaagctgc tgttcgacta caacctgctg accgaccaca 1200
gcgagctgag cggcatcaac ccctacgagg ccagagtgaa gggcctgagc cagaagctga 1260
gcgaggaaga gttctctgcc gccctgctgc acctggccaa gagaagaggc gtgcacaacg 1320
tgaacgaggt ggaagaggac accggcaacg agctgtccac caaagagcag atcagccgga 1380
acagcaaggc cctggaagag aaatacgtgg ccgaactgca gctggaacgg ctgaagaaag 1440
acggcgaagt gcggggcagc atcaacagat tcaagaccag cgactacgtg aaagaagcca 1500

-continued

```
aacagctgct gaaggtgcag aaggcctacc accagctgga ccagagcttc atcgacacct   1560
acatcgacct gctggaaacc cggcggacct actatgaggg acctggcgag ggcagcccct   1620
tcggctggaa ggacatcaaa gaatggtacg agatgctgat gggccactgc acctacttcc   1680
ccgaggaact gcggagcgtg aagtacgcct acaacgccga cctgtacaac gccctgaacg   1740
acctgaacaa tctcgtgatc accagggacg agaacgagaa gctggaatat tacgagaagt   1800
tccagatcat cgagaacgtg ttcaagcaga agaagaagcc caccctgaag cagatcgcca   1860
aagaaatcct cgtgaacgaa gaggatatta agggctacag agtgaccagc accggcaagc   1920
ccgagttcac caacctgaag gtgtaccacg acatcaagga cattaccgcc cggaaagaga   1980
ttattgagaa cgccgagctg ctggatcaga ttgccaagat cctgaccatc taccagagca   2040
gcgaggacat ccaggaagaa ctgaccaatc tgaactccga gctgacccag gaagagatcg   2100
agcagatctc taatctgaag ggctataccg gcacccacaa cctgagcctg aaggccatca   2160
acctgatcct ggacgagctg tggcacacca acgacaacca gatcgctatc ttcaaccggc   2220
tgaagctggt gcccaagaag gtggacctgt cccagcagaa agagatcccc accaccctgg   2280
tggacgactt catcctgagc cccgtcgtga agagaagctt catccagagc atcaaagtga   2340
tcaacgccat catcaagaag tacggcctgc ccaacgacat cattatcgag ctggcccgcg   2400
agaagaactc caaggacgcc cagaaaatga tcaacgagat gcagaagcgg aaccggcaga   2460
ccaacgagcg gatcgaggaa atcatccgga ccaccggcaa agagaacgcc aagtacctga   2520
tcgagaagat caagctgcac gacatgcagg aaggcaagtg cctgtacagc ctggaagcca   2580
tccctctgga agatctgctg aacaacccct tcaactatga ggtggaccac atcatcccca   2640
gaagcgtgtc cttcgacaac agcttcaaca acaaggtgct cgtgaagcag gaagaagcca   2700
gcaagaaggg caaccggacc ccattccagt acctgagcag cagcgacagc aagatcagct   2760
acgaaacctt caagaagcac atcctgaatc tggccaaggg caagggcaga atcagcaaga   2820
ccaagaaaga gtatctgctg gaagaacggg acatcaacag gttctccgtg cagaaagact   2880
tcatcaaccg gaacctggtg gataccagat acgccaccag aggcctgatg aacctgctgc   2940
ggagctactt cagagtgaac aacctggacg tgaaagtgaa gtccatcaat ggcggcttca   3000
ccagctttct gcggcggaag tggaagttta agaaagagcg gaacaagggg tacaagcacc   3060
acgccgagga cgccctgatc attgccaacg ccgatttcat cttcaaagag tggaagaaac   3120
tggacaaggc caaaaaagtg atggaaaacc agatgttcga ggaaaagcag gccgagagca   3180
tgcccgagat cgaaaccgag caggagtaca aagagatctt catcaccccc caccagatca   3240
agcacattaa ggacttcaag gactacaagt acagccaccg ggtggacaag aagcctaata   3300
gagagctgat taacgacacc ctgtactcca cccggaagga cgacaagggc aacaccctga   3360
tcgtgaacaa tctgaacggc ctgtacgaca aggacaatga caagctgaaa aagctgatca   3420
acaagagccc cgaaaagctg ctgatgtacc accacgaccc ccagacctac cagaaactga   3480
agctgattat ggaacagtac ggcgacgaga agaatcccct gtacaagtac tacgaggaaa   3540
ccgggaacta cctgaccaag tactccaaaa aggacaacgg ccccgtgatc aagaagatta   3600
agtattacgg caacaaactg aacgcccatc tggacatcac cgacgactac cccaacagca   3660
gaaacaaggt cgtgaagctg tccctgaagc cctacagatt cgacgtgtac ctggacaatg   3720
gcgtgtacaa gttcgtgacc gtgaagaatc tggatgtgat caaaaaagaa aactactacg   3780
aagtgaatag caagtgctat gaggaagcta agaagctgaa gaagatcagc aaccaggccg   3840
agtttatcgc ctccttctac aacaacgatc tgatcaagat caacggcgag ctgtatagag   3900
```

```
tgatcggcgt gaacaacgac ctgctgaacc ggatcgaagt gaacatgatc gacatcacct   3960
accgcgagta cctggaaaac atgaacgaca agaggccccc caggatcatt aagacaatcg   4020
cctccaagac ccagagcatt aagaagtaca gcacagacat tctgggcaac ctgtatgaag   4080
tgaaatctaa gaagcaccct cagatcatca aaaagggcaa aaggccggcg gccacgaaaa   4140
aggccggcca ggcaaaaaag aaaaagggat ccgacgcgct ggacgatttc gatctcgaca   4200
tgctgggttc tgatgccctc gatgactttg acctggatat gttgggaagc gacgcattgg   4260
atgactttga tctggacatg ctcggctccg atgctctgga cgatttcgat ctcgatatgt   4320
tataagaatt catcgatacc gtcgagatct aacttgttta ttgcagctta taatggttac   4380
aaataaagca atagcatcac aaatttcaca aataaagcat ttttttcact gcattctagt   4440
tgtggtttgt ccaaactcat caatgtatct tatcatgtct ggaggtaccg agggcctatt   4500
tcccatgatt ccttcatatt tgcatatacg atacaaggct gttagagaga taattggaat   4560
taatttgact gtaaacacaa agatattagt acaaaatacg tgacgtagaa agtaataatt   4620
tcttgggtag tttgcagttt taaaattatg ttttaaaatg gactatcata tgcttaccgt   4680
aacttgaaag tatttcgatt tcttggcttt atatatcttg tggaaaggac gaaacaccga   4740
tcatgcgaaa ggggagctgt gttttagtac tctggaaaca gaatctacta aaacaaggca   4800
aaatgccgtg tttatctcgt caacttgttg gcgagatttt tgcggccgca ggaaccccta   4860
gtgatggagt tggccactcc ctctctgcgc gctcgctcgc tcactgaggc cgggcgacca   4920
aaggtcgccc gacgcccggg ctttgcccgg gcggcctcag tgagcgagcg agcgcgcagc   4980
tgcctgcagg ggcgcctgat gcggtatttt ctccttacgc atctgtgcgg tatttcacac   5040
cgcatacgtc aaagcaacca tagtacgcgc cctgtagcgg cgcattaagc gcggcgggtg   5100
tggtggttac gcgcagcgtg accgctacac ttgccagcgc cttagcgccc gctcctttcg   5160
ctttcttccc ttcctttctc gccacgttcg ccggctttcc ccgtcaagct ctaaatcggg   5220
ggctcccttt agggttccga tttagtgctt tacggcacct cgaccccaaa aaacttgatt   5280
tgggtgatgg ttcacgtagt gggccatcgc cctgatagac ggtttttcgc cctttgacgt   5340
tggagtccac gttctttaat agtggactct tgttccaaac tggaacaaca ctcaactcta   5400
tctcgggcta ttcttttgat ttataaggga ttttgccgat ttcggtctat tggttaaaaa   5460
atgagctgat ttaacaaaaa tttaacgcga attttaacaa aatattaacg tttacaattt   5520
tatggtgcac tctcagtaca atctgctctg atgccgcata gttaagccag ccccgacacc   5580
cgccaacacc cgctgacgcg ccctgacggg cttgtctgct cccggcatcc gcttacagac   5640
aagctgtgac cgtctccggg agctgcatgt gtcagaggtt ttcaccgtca tcaccgaaac   5700
gcgcgagacg aaagggcctc gtgatacgcc tatttttata ggttaatgtc atgataataa   5760
tggtttctta gacgtcaggt ggcacttttc ggggaaatgt gcgcggaacc cctatttgtt   5820
tatttttcta aatacattca aatatgtatc cgctcatgag acaataaccc tgataaatgc   5880
ttcaataata ttgaaaaagg aagagtatga gtattcaaca tttccgtgtc gcccttattc   5940
ccttttttgc ggcattttgc cttcctgttt ttgctcaccc agaaacgctg gtgaaagtaa   6000
aagatgctga agatcagttg ggtgcacgag tgggttacat cgaactggat ctcaacagcg   6060
gtaagatcct tgagagtttt cgccccgaag aacgttttcc aatgatgagc acttttaaag   6120
ttctgctatg tggcgcggta ttatcccgta ttgacgccgg gcaagagcaa ctcggtcgcc   6180
gcatacacta ttctcagaat gacttggttg agtactcacc agtcacagaa aagcatctta   6240
```

-continued cggatggcat gacagtaaga gaattatgca gtgctgccat aaccatgagt gataacactg 6300
cggccaactt acttctgaca acgatcggag gaccgaagga gctaaccgct tttttgcaca 6360
acatggggga tcatgtaact cgccttgatc gttgggaacc ggagctgaat gaagccatac 6420
caaacgacga gcgtgacacc acgatgcctg tagcaatggc aacaacgttg cgcaaactat 6480
taactggcga actacttact ctagcttccc ggcaacaatt aatagactgg atggaggcgg 6540
ataaagttgc aggaccactt ctgcgctcgg cccttccggc tggctggttt attgctgata 6600
aatctggagc cggtgagcgt ggaagccgcg gtatcattgc agcactgggg ccagatggta 6660
agccctcccg tatcgtagtt atctacacga cggggagtca ggcaactatg gatgaacgaa 6720
atagacagat cgctgagata ggtgcctcac tgattaagca ttggtaactg tcagaccaag 6780
tttactcata tatactttag attgatttaa aacttcattt ttaatttaaa aggatctagg 6840
tgaagatcct ttttgataat ctcatgacca aaatccctta acgtgagttt tcgttccact 6900
gagcgtcaga ccccgtagaa aagatcaaag gatcttcttg agatcctttt tttctgcgcg 6960
taatctgctg cttgcaaaca aaaaaaccac cgctaccagc ggtggtttgt ttgccggatc 7020
aagagctacc aactcttttt ccgaaggtaa ctggcttcag cagagcgcag ataccaaata 7080
ctgttcttct agtgtagccg tagttaggcc accacttcaa gaactctgta gcaccgccta 7140
catacctcgc tctgctaatc ctgttaccag tggctgctgc cagtggcgat aagtcgtgtc 7200
ttaccgggtt ggactcaaga cgatagttac cggataaggc gcagcggtcg ggctgaacgg 7260
ggggttcgtg cacacagccc agcttggagc gaacgaccta caccgaactg agatacctac 7320
agcgtgagct atgagaaagc gccacgcttc ccgaagggag aaaggcggac aggtatccgg 7380
taagcggcag ggtcggaaca ggagagcgca cgagggagct tccaggggga aacg 7434

<210> SEQ ID NO 12
<211> LENGTH: 11
<212> TYPE: PRT
<213> ORGANISM: Artificial Sequence
<220> FEATURE:
<223> OTHER INFORMATION: Dp427c Nterm

<400> SEQUENCE: 12

Met Leu Trp Trp Glu Glu Val Glu Asp Cys Tyr
1 5 10

<210> SEQ ID NO 13
<211> LENGTH: 7
<212> TYPE: PRT
<213> ORGANISM: Artificial Sequence
<220> FEATURE:
<223> OTHER INFORMATION: Dp427p Nterm

<400> SEQUENCE: 13

Met Ser Glu Val Ser Ser Asp
1 5

COMPOSITIONS AND METHODS FOR UPREGULATING ISOFORMS OF DYSTROPHIN AS THERAPY FOR DUCHENNE MUSCULAR DYSTROPHY (DMD)

CROSS-REFERENCE TO RELATED APPLICATION

The present application is a 35 U.S.C. § 371 national phase application from, and claims priority to, International Application No. PCT/US2020/055089, filed Oct. 9, 2020, and is entitled to priority under 35 U.S.C. § 119 (e) to U.S. Provisional Patent Application No. 62/913,935, filed Oct. 11, 2019, and U.S. Provisional Patent Application No. 63/064,077, filed Aug. 11, 2020, all of which are hereby incorporated by reference in their entireties herein.

SEQUENCE LISTING

The instant application contains a Sequence Listing which has been submitted in ASCII format via EFS-Web and is hereby incorporated by reference in its entirety. Said ASCII copy, created on Apr. 8, 2022, is named "047162-7245US1 (01236) SequenceListing_ST25" and is 12.1 kilobytes in size.

BACKGROUND OF THE INVENTION

Duchenne muscular dystrophy (DMD) is a genetic disorder characterized by progressive muscle degeneration and weakness. It is one of nine types of muscular dystrophy. DMD is caused by an absence of dystrophin, a protein that helps keep muscle cells intact. Symptom onset is in early childhood, usually between ages 3 and 5. The disease primarily affects boys, but in rare cases it can affect girls. Muscle weakness can begin as early as age 3, first affecting the muscles of the hips, pelvic area, thighs and shoulders, and later the skeletal (voluntary) muscles in the arms, legs and trunk. The calves often are enlarged. By the early teens, the heart and respiratory muscles also are affected. Becker muscular dystrophy (BMD) is a milder version of DMD. Its onset is usually in the teens or early adulthood, and the course is slower and less predictable than that of DMD. BMD is similar to DMD but allows the voluntary muscles to function better than they do in DMD. The heart muscle, however, can be affected similarly to the way it is in DMD. DMD and BMD are thought to be caused by a mutation in the dystrophin gene. Lack of the dystrophin protein in muscle cells causes them to be fragile and easily damaged.

Current gene therapy strategies for DMD include exon skipping using antisense oligonucleotides (ASOs) and restoration of dystrophin expression using a 'mini dystrophin' construct delivered using AAV. Due to the packaging limit of AAV, not all functional domains of dystrophin can be included (mini-dystrophin). This approach at best improves a DMD patient pathology into a Becker Muscular Dystrophy (BMD) pathology, which still results in significant morbidity.

A need exists for compositions and methods for treating DMD, especially those that result in functional restoration or expression of full-length dystrophin. The present invention addresses this need.

SUMMARY OF THE INVENTION

As described herein, the present invention relates to methods for treating a disease or disorder that is associated with aberrant or absent dystrophin, by upregulating a brain isoform of dystrophin (e.g. purkinje and/or cortical) in a subject in need thereof.

In one aspect, the invention provides a method of treating a disease or disorder in a subject in need thereof, wherein the disease or disorder is associated with aberrant or absent dystrophin. The method comprises administering to the subject a composition that upregulates a brain isoform of dystrophin.

In various embodiments of the above aspect or any other aspect of the invention delineated herein, the brain isoform of dystrophin is selected from the group consisting of purkinje and cortical.

In certain embodiments, the disease is Duchenne Muscular Dystrophy (DMD).

In certain embodiments, the disease is X-linked cardiomyopathy.

In certain embodiments, the subject has an absence of muscle dystrophin.

In certain embodiments, the subject has a mutation or deletion in the promoter and/or exon 1 of the muscle dystrophin gene.

In certain embodiments, the composition comprises a CRISPR activation (CRISPRa) system that upregulates the brain isoform of dystrophin. In certain embodiments, the CRISPRa system comprises an AAV vector comprising a tissue-specific promoter. In certain embodiments, the CRISPRa system comprises an AAV vector comprising a muscle-specific promoter. In certain embodiments, the promoter yields expression of the vector in skeletal muscle tissue and/or cardiac tissue. In certain embodiments, the promoter is a muscle creatine kinase 8 (CK8e) promoter.

In certain embodiments, the CRISPRa system comprises a guide RNA that targets the cortical dystrophin promoter region. In certain embodiments, the gRNA target region comprises a nucleotide sequence selected from the group consisting of SEQ ID NO:4-7.

In certain embodiments, the CRISPRa system comprises a guide RNA that targets the purkinje dystrophin promoter region. In certain embodiments, the gRNA target region comprises a nucleotide sequence selected from the group consisting of SEQ ID NO: 8-10.

In certain embodiments, the AAV vector comprises the nucleotide sequence of SEQ ID NO: 11.

In certain embodiments, the CRISPR activation (CRISPRa) system is a single vector system.

In another aspect, the invention provides a pharmaceutical composition comprising an AAV vector comprising an MHCK7 promoter and a gRNA sequence that targets the cortical dystrophin promoter region or the purkinje dystrophin promoter region.

In another aspect, the invention provides a pharmaceutical composition comprising an AAV vector comprising a CK8e promoter and a gRNA sequence that targets the cortical dystrophin promoter region or the purkinje dystrophin promoter region.

In certain embodiments, the AAV vector comprises the nucleotide sequence of SEQ ID NO: 11.

In certain embodiments, the gRNA sequence comprises a nucleotide sequence selected from the group consisting of SEQ ID NO: 4-10.

BRIEF DESCRIPTION OF THE DRAWINGS

The following detailed description of specific embodiments of the invention will be better understood when read in conjunction with the appended drawings. For the purpose of illustrating the invention, there are shown in the drawings exemplary embodiments. It should be understood, however, that the invention is not limited to the precise arrangements and instrumentalities of the embodiments shown in the drawings.

FIG. 2A: Components include an AAV2 backbone and dSaCas9-VP64 from Addgene® plasmid #99680 and a muscle creatine kinase 8 (CK8e) promoter. Components include a U6 promoter and dSaCas9 gRNA scaffold from Addgene® plasmid #99690 and a CK8e. A gRNA spacer was designed, synthesized, and inserted. FIG. 2B: Modified from original Addgene® plasmid #135338 3XFLAG-VP64-SaCas9-NLS-VP64. The native CMV promoter was exchanged for the skeletal and cardiac muscle specific promoter and the 3xFLAG tags were removed. C7 denotes guide RNA sequence insertion under control of U6 promoter.

DETAILED DESCRIPTION

Definitions

Figure 1:
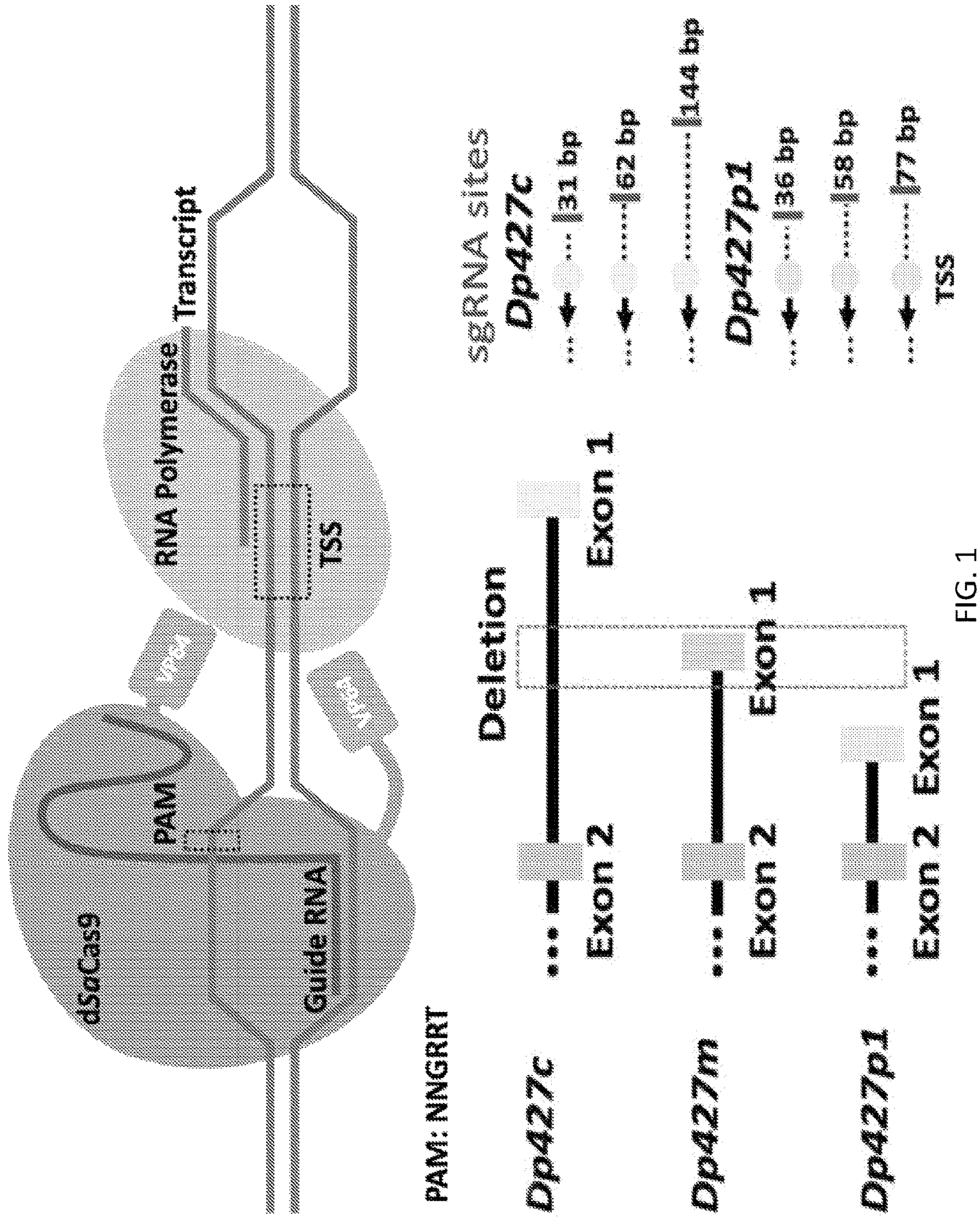
FIG. 1: A generalized schematic depicting the CRISPR-dCas9 activation machinery with two VP64 transactivator domains targeted to the promoter region of cortical (Dp427c) and purkinje (Dp427p1) isoforms of dystrophin.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "cleavage" refers to the breakage of covalent bonds, such as in the backbone of a nucleic acid molecule or the hydrolysis of peptide bonds. Cleavage can be initiated by a variety of methods, including, but not limited to, enzymatic or chemical hydrolysis of a phosphodiester bond. Both single-stranded cleavage and double-stranded cleavage are possible. Double-stranded cleavage can occur as a result of two distinct single-stranded cleavage events. DNA cleavage can result in the production of either blunt ends or staggered ends. In certain embodiments, fusion polypeptides may be used for targeting cleaved double-stranded DNA.

The term "CRISPR/Cas" or "clustered regularly interspaced short palindromic repeats" or "CRISPR" refers to DNA loci containing short repetitions of base sequences followed by short segments of spacer DNA from previous exposures to a virus or plasmid. Bacteria and archaea have evolved adaptive immune defenses termed CRISPR/CRISPR-associated (Cas) systems that use short RNA to direct degradation of foreign nucleic acids. In bacteria, the CRISPR system provides acquired immunity against invading foreign DNA via RNA-guided DNA cleavage.

The "CRISPR/Cas9" system or "CRISPR/Cas9-mediated gene editing" refers to a type II CRISPR/Cas system that has been modified for genome editing/engineering. It is typically comprised of a "guide" RNA (gRNA) and a non-specific CRISPR-associated endonuclease (Cas9). "Guide RNA (gRNA)" is used interchangeably herein with "short guide RNA (sgRNA)" or "single guide RNA (sgRNA). The sgRNA is a short synthetic RNA composed of a "scaffold" sequence necessary for Cas9-binding and a user-defined ~20 nucleotide "spacer" or "targeting" sequence which defines the genomic target to be modified. The genomic target of Cas9 can be changed by changing the targeting sequence present in the sgRNA.

"CRISPRa" system refers to a modification of the CRISPR-Cas9 system that functions to activate or increase gene expression. In certain embodiments, the CRISPRa system is comprised of a catalytically dead RNA/DNA guided endonuclease, such as dCas9, dCas12a/dCpf1, dCas12b/dC2c1, dCas12c/dC2c3, dCas12d/dCasY, dCas12e/dCasX, dCas13a/dC2c2, dCas13b, dCas13c, dead Cascade complex, or others; at least one transcriptional activator; and at least one sgRNA that functions to increase expression of at least one gene of interest. The term "activation" as used herein refers to an increase in gene expression of one or more genes.

"dCas9" as used herein refers to a catalytically dead Cas9 protein that lacks endonuclease activity.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "downregulation" as used herein refers to the decrease or elimination of gene expression of one or more genes.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to, anti-tumor activity as determined by any means suitable in the art.

“Encoding” refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein “endogenous” refers to any material from or produced inside an organism, cell, tissue or system.

As used herein, the term “exogenous” refers to any material introduced from or produced outside an organism, cell, tissue or system.

The term “expression” as used herein is defined as the transcription and/or translation of a particular nucleotide sequence driven by its promoter.

“Expression vector” refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., Sendai viruses, lentiviruses, retroviruses, adenoviruses, and adeno-associated viruses) that incorporate the recombinant polynucleotide.

“Homologous” as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

“Identity” as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

As used herein, an “instructional material” includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

“Isolated” means altered or removed from the natural state. For example, a nucleic acid or a peptide naturally present in a living animal is not “isolated,” but the same nucleic acid or peptide partially or completely separated from the coexisting materials of its natural state is “isolated.” An isolated nucleic acid or protein can exist in substantially purified form, or can exist in a non-native environment such as, for example, a host cell.

The term “knockdown” as used herein refers to a decrease in gene expression of one or more genes.

The term “knockout” as used herein refers to the ablation of gene expression of one or more genes.

A “lentivirus” as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

The term “limited toxicity” as used herein, refers to the peptides, polynucleotides, cells and/or antibodies of the invention manifesting a lack of substantially negative biological effects, anti-tumor effects, or substantially negative physiological symptoms toward a healthy cell, non-tumor cell, non-diseased cell, non-target cell or population of such cells either in vitro or in vivo.

By the term “modified” as used herein, is meant a changed state or structure of a molecule or cell of the invention. Molecules may be modified in many ways, including chemically, structurally, and functionally. Cells may be modified through the introduction of nucleic acids.

By the term “modulating,” as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

In the context of the present invention, the following abbreviations for the commonly occurring nucleic acid bases are used. “A” refers to adenosine, “C” refers to cytosine, “G” refers to guanosine, “T” refers to thymidine, and “U” refers to uridine.

Unless otherwise specified, a “nucleotide sequence encoding an amino acid sequence” includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

A "target site" or "target sequence" refers to a genomic nucleic acid sequence that defines a portion of a nucleic acid to which a binding molecule may specifically bind under conditions sufficient for binding to occur.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

To "treat" a disease as the term is used herein, means to reduce the frequency or severity of at least one sign or symptom of a disease or disorder experienced by a subject.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, Sendai viral vectors, adenoviral vectors, adeno-associated virus vectors, retroviral vectors, lentiviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention is based on the unexpected finding that upregulating the brain isoforms of dystrophin (cortical and purkinje) can compensate for the absence of muscle dystrophin in DMD patients as well as in X-linked cardiomyopathy patients who have mutations in the promoter and/or exon 1 of muscle dystrophin.

Dystrophin is encoded by the DMD gene, which produces a range of different transcripts encoding various dystrophin isoforms, i.e. proteins of varying lengths containing different segments of the basic dystrophin sequence. The isoforms are encoded by a range of different mRNAs which are generated by three processes: i.) the use of different, unique and often tissue-specific promoters, ii.) alternative splicing, and iii.) the use of different polyA-addition signals. The main dystrophin protein found in muscle is designated Dp427m. Its exon 1 encodes a unique N-terminal MLWWEEVEDCY amino acid sequence (SEQ ID NO: 12). Dp427m is also expressed in skeletal muscle and the heart.

The purkinje isoform, Dp427p, initiates from a unique promoter/exon 1 which is located in the first intron of the Dp427m gene. The Purkinje promoter drives nearly all cerebellar dystrophin expression. The transcript splices directly into the common exon 2 of Dp427m and has a similar length, i.e. 14 kb. Dp427p contains a unique N-terminal MSEVSSD amino acid sequence (SEQ ID NO: 13), exchanging the MLWWEEVEDCY-start (SEQ ID NO: 12) of Dp427m. The remainder of Dp427p is identical to Dp427m. Two alternatively spliced Dp427p transcripts were detected in cortical brain and adult skeletal muscle and, at much lower levels, in adult cardiac tissue. The two alternatively spliced transcripts, designated Dp427p1 and Dp427p2, differed by the insertion of 82 nucleotides directly flanking Dp427p exon 1. The 82 nucleotides insertion in Dp427p2 introduces a translational stop codon 24 bp downstream of the ATG-codon used in Dp427p1; it is unclear whether any protein is generated from this transcript. Dp427p1 is the predominant transcript in fetal brain, Dp427p2 in adult brain. Fetal skeletal muscle contains low, but equal levels of Dp427p1 and Dp427p2 while adult skeletal muscle contains mainly Dp427p1. Dp427p is up-regulated in skeletal muscle, but not cardiac muscle, of XLDC-patients with mutations in the Dp427m promoter/exon 1.

The cortical isoform, Dp427c, is expressed predominantly in neurons of the cortex and the CA regions of the hippocampus. It uses a unique promoter/exon 1, located about 130 kb upstream of the muscle promoter. The cortical promoter does not contain typical transcription elements and has no TATA-box. The transcript splices directly into the common exon 2 of Dp427m and has a similar length, i.e. 14 kb. Dp427c contains a unique N-terminal MED amino acid sequence, exchanging the MLWWEEVEDCY-start (SEQ ID NO: 12) of Dp427m. The remainder of Dp427c is identical to Dp427m. Total dystrophin expression levels in brain are in the range of 1-2% of those in muscle. Using RT-PCR, Dp427c expression is detectable in heart muscle but hardly in adult skeletal muscle. The Dp427c isoform is also known as brain dystrophin. Dp427c is up-regulated in skeletal muscle, but not cardiac muscle, of XLDC-patients with mutations in the Dp427m promoter/exon 1.

Methods of Treatment

Provided herein is a method for treating a disease or disorder that is associated with aberrant or absent dystrophin. The method comprises administering to a subject a composition that upregulates a brain isoform of dystrophin (e.g. cortical and/or purkinje isoforms). Any disease or disorder wherein dystrophin is not functioning properly can be treated with the method of the invention. For example, the method described herein can be used to treat Duchenne Muscular Dystrophy (DMD). In certain embodiments, the method can treat X-linked cardiomyopathy. In certain embodiments, the method can be used to upregulate a muscle-specific isoform of dystrophin in Becker Muscular Dystrophy (BMD) linked to reduced levels of dystrophin expression due to predominately in-frame deletions/duplications.

In certain embodiments, the subject to be treated has an absence of muscle dystrophin. In certain embodiments, the subject has a mutation or deletion in the promoter and/or exon 1 of the muscle dystrophin gene.

Any method known to one of ordinary skill in the art may be used to upregulate the brain isoform of dystrophin. For example, methods that upregulate gene expression include, but are not limited to, micro RNA (miRNA), epigenetic modulators, histone deacetylase inhibitors (HDACIs).

In certain embodiments, the method utilizes a CRISPR activation system (CRISPRa) to upregulate the brain isoform of dystrophin. For example, in certain embodiments, the method utilizes dCas9 (deactivated Cas9) and fusion with transcriptional activators such as VPR (VP64-p65-Rta), VP64, SAM (synergistic activation mediator, MS2-p65-HSF1), and Suntag activators. In certain embodiments, a composition comprising a CRISPRa system is administered to the subject to upregulate a brain isoform of dystrophin.

In certain embodiments, the CRISPRa system comprises an AAV vector comprising a tissue-specific promoter. In certain embodiments, the promoter is a muscle-specific promoter. Examples of muscle-specific promoters include, but are not limited to, a truncated version of muscle creatine kinase (Cordier et. al. (2001) *Hum Gene Ther*. January 20; 12(2):205-15), dMCK, tMCK (Wang et. al. (2008) *Gene Ther*. November; 15(22):1489-99, and muscle-specific promoters derived from the genetic elements of the human slow isoform of troponin I gene (TnIS) including constructs containing one to four copies of the TnIS upstream enhancer (USE) or truncated USE (δUSE) fused to the minimal promoter of the TnIS gene (Zeng et al. *Molecular Therapy* Volume 16, SUPPLEMENT 1, S198, May 1, 2008). In certain embodiments, the promoter yields expression of the vector in skeletal muscle tissue. In certain embodiments, the promoter yields expression of the vector in cardiac tissue. In certain embodiments, the promoter is a MHCK7 promoter. In certain embodiments, the promoter is a muscle creatine kinase 8 (CK8e) promoter (Amoasii et al. *Science*. 2018 Oct.

5; 362(6410): 86-91; Salva et al. *Molecular Therapy* vol. 15 no. 2, 320-329 February 2007)).

In certain embodiments, the CRISPRa system comprises a guide RNA that targets the cortical dystrophin promoter region. In certain embodiments, the gRNA target region comprises a nucleotide sequence selected from the group consisting of SEQ ID NO: 4-7.

In certain embodiments, the CRISPRa system comprises a guide RNA that targets the purkinje dystrophin promoter region. In certain embodiments, the gRNA target region comprises a nucleotide sequence selected from the group consisting of SEQ ID NO: 8-10.

In certain embodiments, the guide RNA is administered as a separate nucleic acid (e.g. plasmid) than the other components of the CRISPRa system (e.g. Cas9, transactivators, etc.). In certain embodiments, all of the components of the CRISPRa system are included in a single nucleic acid (e.g. a single vector), and as such a single nucleic acid is administered to the subject for treatment.

In certain embodiments, a subject is administered a single vector for treatment of a disease or disorder that is associated with aberrant or absent dystrophin. The method comprises upregulating a brain isoform of dystrophin. In certain embodiments, the vector comprises the nucleotide sequence of SEQ ID NO: 11 (double VP64 backbone with C7 guide).

In certain embodiments, a CRISPRa construct may be used to upregulate a muscle dystrophin isoform to treat a dystrophin-deficient condition (e.g. DMD, BMD, and/or X-linked dilated cardiomyopathy (XLDCM)).

CRISPR Activation (CRISPRa) System

The CRISPR activation (CRISPRa) system is comprised of a catalytically inactive RNA-guided endonuclease or other endonucleases, such as but not limited to dCas9, dSaCas9, dCas12a/dCpf1, dCas12b/dC2c1, dCas12c/dC2c3, dCas12d/dCasY, dCas12e/dCasX, dCas13a/dC2c2, dCas13b, dCas13c, dead Cascade complex, or others. The CRISPRa system also comprises at least one transcriptional activator, and at least one guide RNA (gRNA) and functions to increase expression of at least one gene of interest. Like a standard CRISPR-Cas9 system, CRISPRa systems rely on gRNAs to guide dCas9 to intended targets. However, while a standard CRISPR-Cas9 system creates breaks in DNA through the endonuclease activity of Cas9 and then manipulates DNA repair mechanisms for gene editing, CRISPRa systems are modified and employ transcriptional activators to increase expression of a gene or multiple genes of interest.

"dCas9" refers to a catalytically dead Cas9 protein that lacks endonuclease activity. This can be accomplished by introducing point mutations in the two catalytic residues (D10A and H840A) of the gene encoding Cas9. In doing so, dCas9 is unable to cleave dsDNA but retains the ability to target and bind DNA. This alone is often enough to attenuate if not outright block transcription of the targeted gene if the gRNA positions dCas9 in a way that prevents transcriptional factors and RNA polymerase from accessing the DNA. However, this ability to bind DNA can also be exploited for activation since dCas9 has modifiable regions, typically the N and C terminus of the protein, that can be used to attach transcriptional activators.

Targeting specificity is determined by complementary base-pairing of a small guide RNA (gRNA or sgRNA) to the genomic loci. gRNA is a chimeric noncoding RNA that can be subdivided into three regions: a base-pairing sequence, a dCas9-binding hairpin and a terminator. When designing a synthetic gRNA, only the base-pairing sequence is modified. Secondary variables must also be considered: off-target effects (for which a simple BLAST run of the base-pairing sequence is required), maintenance of the dCas9-binding hairpin structure, and ensuring that no restriction sites are present in the modified gRNA, as this may pose a problem in downstream cloning steps. dCas9 can be derived, for example, from *S. pyogenes*, *S. aureus* (dSaCas9), *N. meningiditis*, *S. thermopilus*, *F. novicida*, *C. jejuni*, *B. laterosporus*, or from other species.

Transcriptional activators are protein domains or whole proteins that can be linked to dCas9 or gRNAs and assist in the recruitment of important co-factors as well as RNA Polymerase for transcription of the gene(s) targeted by the system. Transcriptional activators have a DNA binding domain and a domain for activation of transcription. The activation domain can recruit general transcription factors or RNA polymerase to the gene sequence. Activation domains can also function by facilitating transcription by stalled RNA polymerases, and in eukaryotes can act to move nucleosomes on the DNA or modify histones to increase gene expression. These activators can be introduced into the system through attachment to dCas9 or to the gRNA. Transcriptional activators can be either mammalian cellular endogenous proteins that have activator function, activators from other species such as viruses, microbials or plants, their partial or mutant variants, engineered activators, or other forms of activators that can increase gene expression. A list of applicable viral activators include but are not limited to: VP16, VP32, VP64, VP160, HBx, NS proteins, and VMW65. A list of applicable microbial activators include but are not limited to: Lac operons and GAL4. A list of applicable mammalian cellular transcriptional activators include but are not limited to: CAP, ACTN1, ACTN2, ACTN2, ACTN4, ACTN4, ANKRD1, APEX1, ARID5B, ARL2BP, ASCC1, ASXL1, ATN1, ATXN7L3, ATXN7L3, ATXN7L3, BCL9, BCL9L, BCL10, BCL10, BICRA, BIRC2, BRCA1, BRD7, CALCOCO1, CALCOCO1, CALCOCO1, CALCOCO1, CARM1, CARM1, CARM1, CBFB, CCAR1, CCAR1, CCAR1, CCAR1, CCAR2, CCDC62, CEBPA, CENPJ, CITED1, CITED1, CITED2, CITED2, CITED2, CITED2, CITED2, CITED4, CITED4, CITED4, COPS5, CREBBP, CREBBP, CREBBP, CTBP2, CTNNB1, CTNNB1, CTNNB1, CTNNB1, CTNNB1, DAXX, DAXX, DCAF6, DCC, DDX17, DHX9, DR1, DYRK1B, EDF1, ELF3, ELOB, ENY2, ENY2, ENY2, EP300, EP300, EP300, FAM129B, FGF2, FHL5, FOXC1, GATA3, GATA3, GATA3, GATA4, GM20517, GMEB1, GMEB2, GPS2, GPS2, GTF2A2, GTF2A2, HAND1, HCFC1, HCFC1, HELZ2, HIF3A, HINFP, HIPK2, HMGA1, HMGA1, HMGA1B, HMGB2, HYAL2, ING4, ISL1, JADE1, JMJD6, JMY, JMY, JUN, JUN, JUNB, JUND, JUP, JUP, KAT2A, KAT2B, KAT2B, KAT5, KAT5, KAT6A, KDM1A, KDM5A, KMT2C, KMT2D, LPIN1, LPIN1, LPIN2, LPIN2, LPIN3, MAGED1, MAK, MAML1, MAML1, MAML1, MAML1, MAML2, MAML2, MAML3, MAML3, MAML3, MCIDAS, MED1, MED1, MED1, MED1, MED1, MED1, MED6, MED12, MED12, MED12, MED12L, MED13, MED14, MED16, MED17, MED17, MED20, MED21, MED24, MED27, MED31, MEF2A, MMS19, MRTFA, MRTFB, MRTFB, MTA1, MTA1, MTA1, MTA1, MTA2, MTA3, MTDH, MYCBP, MYOCD, MYOD1, MYSM1, MYT1L, NACA, NCOA1, NCOA1, NCOA1, NCOA1, NCOA1, NCOA2, NCOA2, NCOA2, NCOA2, NCOA2, NCOA2, NCOA3, NCOA3, NCOA3, NCOA3, NCOA3, NCOA6, NCOA6, NCOA7, NEUROD1, NEUROG3, NFE2L1, NKX2-2, NME2, NPAT, NPM1, NR1D1, NR1D2, NR1H2, NR1H3, NR1H3, NR1H4, NR1H5, NR1I2, NR1I3, NR3C1, NRBF2, NRIP1, NRIP1, NRIP1, NRL, NSD3, NUP98, NUPR1, PARK7, PCBD1, PDLIM1, PER2, PHF2, PKN1, PMF1, PMF1, PML, PML, PML, POU2AF1, POU3F1, POU3F2, POU3F2, POU4F1, POU4F2, POU5F1, PPARA, PPARD, PPARD, PPARG, PPARG, PPARG, PPARGC1A, PPARGC1A, PPARGC1A, PPARGC1A, PPARGC1A, PPARGC1A, PPARGC1B, PPARGC1B, PPRC1, PRDM16, PRKCB, PRMT2, PRPF6, PRRX1, PSIP1, PSMC3IP, PSMC3IP, PSMD9, PSMD9, PUS1, RAP2C, RARA, RARA, RARB, RARG, RBM14, RBM14, RBM39, RBPMS, RERE, REXO4, RNF20, RRP1B, RUVBL1, RXRB, SCAND1, SERTAD2, SETD3, SFR1, SFR1, SIX3, SLC30A9, SLC30A9, SMARCA2, SMARCA4, SMARCB1, SMARCB1, SMARCD3, SNW1, SNW1, SOX4, SOX11, SOX11, SOX12, SOX17, SP4, SRA1, SRA1, SRA1, SRA1, SRA1, SRA1, SS18, SS18, SS18L1, SS18L2, SUB1, SUB1, SUPT3, SUPT7L, TADA1, TADA1, TADA2A, TADA2B, TADA3, TADA3, TADA3, TAF1, TAF5L, TAF6L, TAF6L, TAF7, TAF7, TAF7L, TAF9, TAF11, TAF11, TAF12, TCF3, TDRD3, TFAP2A, TFAP2A, TFAP2A, TFAP2B, TFAP2B, TFAP2B, TGFB1I1, THRA, THRAP3, THRAP3, THRAP3, THRB, TRIM24, TRIM24, TRIM28, TRIP4, TRIP4, TRRAP, TSG101, UBE2L3, UBE3A, USP16, USP21, USP22, USP22, UTF1, UTF1, VDR, VGLL2, WBP2, WBP2, WBP2NL, WDR77, WNT3A, WWC1, WWOX, WWTR1, WWTR1, YAF2, YAP1, YAP1, ZBTB18, ZCCHC12, ZCCHC12, ZCCHC18, ZMIZ2.

One example of a transcriptional activator (or transactivator domain) is VP64. VP64 is made up of four copies of VP16, a viral protein sequence of 16 amino acids that is used for transcriptional activation. Embodiments of the invention include various forms of VP64, for example a nucleic acid comprising dCas9 and/or VP64, or plasmids or vectors that encode the dCas9 and/or VP64 genes. Additional elements can be present in the nucleic acid encoding dCas9 and/or VP64, such as nucleic acids encoding the transcription factors p65 and Rta. Certain embodiments of the invention utilize the VP64-p65-Rta, or VPR, in which a VP64 transcriptional activator is joined to the C terminus of dCas9 and the transcription factors p65 and Rta are added to the C terminus of dCas9-VP64. Therefore, all three transcription factors are targeted to the same gene. The use of three transcription factors, as opposed to solely VP64, results in increased expression of targeted genes. dCas9-VPR can be used to increase expression of multiple genes within the same cell by putting multiple gRNAs into the same cell.

The invention should be construed to work with any alternative activator, such as VP16, VP160, p65AD, p300 or any other transcriptional activator.

The invention should also be construed to work with any dCas9/CRISPRa system or any other adaptor system known in the art, including but not limited to: 1) VP64-p65-Rta (VPR); 2) Synergistic Activation Mediator (SAM) system, which makes use of not only VP64 but also sgRNA 2.0, which contains a sequence to recruit a viral protein fused to even more effectors (p65-hsf1); 3) Suntag, which sports a protruding chain of 10 peptide epitopes that are recognized by an entourage of antibodies fused to VP64; 4) RNA Scaffolds, which also utilize sgRNA 2.0 and recruits 3 viral proteins fused to VP64; 5) The epigenetic editor p300, which deposits activating H3K27ac; 6) VP160, which is also known as CRISPR-on and has ten times the VPs of VP16; and 7) VP64-dCas9-BFP-VP64, which makes use of the neglected N-terminus.

Pharmaceutical Compositions

Provided in the invention are pharmaceutical compositions for treating a disease or disorder that is associated with aberrant or absent dystrophin in a subject in need thereof. In certain aspects, the invention includes a pharmaceutical composition comprising an AAV vector comprising an MHCK7 promoter and a gRNA sequence that targets the cortical dystrophin promoter region or the purkinje dystrophin promoter region. In certain aspects, the invention includes a pharmaceutical composition comprising an AAV vector comprising a CK8e promoter and a gRNA sequence that targets the cortical dystrophin promoter region or the purkinje dystrophin promoter region. In certain embodiments, the AAV vector is used to upregulate cortical dystrophin with the C7 guide. In certain embodiments, the AAV vector comprises the nucleotide sequence set forth in SEQ ID NO: 11. In certain embodiments, the gRNA sequence comprises a nucleotide sequence selected from the group consisting of SEQ ID NOs: 4-10.

Pharmaceutical compositions of the present invention may comprise the AAV vector as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

Compositions of the invention can be administered in dosages and routes and at times to be determined in appropriate pre-clinical and clinical experimentation and trials. Compositions may be administered multiple times at dosages within these ranges. Administration of the pharmaceutical composition of the invention may be combined with other methods useful to treat the desired disease or condition as determined by those of skill in the art.

The administration of the pharmaceutical composition of the invention may be carried out in any convenient manner known to those of skill in the art. For example, pharmaceutical composition of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In other instances, the pharmaceutical composition of the invention is injected directly into a site of inflammation in the subject, a local disease site in the subject, a lymph node, an organ, a tumor, and the like.

In certain embodiments, the pharmaceutical composition may be delivered by a nanoparticle delivery method. Any nanoparticle delivery method known to one of ordinary skill in the art can be used.

It should be understood that the method and pharmaceutical compositions that would be useful in the present invention are not limited to the particular formulations set forth in the examples. The following examples are put forth so as to provide those of ordinary skill in the art with a complete disclosure and description of how to make and use the invention, and are not intended to limit the scope of what the inventors regard as their invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Babar, 2011); "Current Protocols in Immunology" (Coligan, 2002). These techniques are applicable to the production of the polynucleotides and polypeptides of the invention, and, as such, may be considered in making and practicing the invention. Particularly useful techniques for particular embodiments will be discussed in the sections that follow.

EXPERIMENTAL EXAMPLES

The invention is now described with reference to the following Examples. These Examples are provided for the purpose of illustration only, and the invention is not limited to these Examples, but rather encompasses all variations that are evident as a result of the teachings provided herein.

The materials and methods employed in these experiments are now described.

Vector construction: Addgene® plasmids #99680 and #135338 were modified to generate two classes of activation constructs with one or two VP64 domains, and included one or more of the following sgRNA sequences:

Muscle Dystrophin Promoter Targeting Guides:

Guide 1:
(SEQ ID NO: 1)
gAGTGAGTGATCCCAACACTGA

Guide 2:
(SEQ ID NO: 2)
gTGAAATATCCGGGGGCCTCTA

-continued

Guide 3:
(SEQ ID NO: 3)
gCACTTGCTTGTGCGCAGGTCC

Cortical Dystrophin Promoter Targeting Guides:

Guide 1 (C4):
(SEQ ID NO: 4)
GCTTTGCATCTGTACAGAAGA

Guide 2 (C6):
(SEQ ID NO: 5)
gTCGACTGACGTATCAGATAGT

Guide 3 (C7):
(SEQ ID NO: 6)
gATCATGCGAAAGGGGAGCTGT

Guide 4 (C8):
(SEQ ID NO: 7)
GGCATGCCCACCTAACCTAAC

Purkinje Dystrophin Promoter Targeting Guides:

Guide 1:
(SEQ ID NO: 8)
gCACCTCACTATTCACGGCAAC

Guide 2:
(SEQ ID NO: 9)
gAAGAAACCATTGCTGTGAGAG

Guide 3:
(SEQ ID NO: 10)
gAACTGTGTCGTCTGCTTTATA

Additionally, the original CMV promoter in the vector was exchanged for a skeletal and cardiac muscle specific promoter (CK8e).

Addgene® plasmid #99680 was modified to generate new AAV vector constructs that included one or more of the above sgRNA sequences. The original promoter was exchanged for the muscle and heart tissue-specific muscle creatine kinase 8 (CK8e) promoter.

Addgene® plasmid #99690 was modified to generate new AAV vector constructs that included one or more of the above sgRNA sequences. The original promoter was exchanged for the muscle and heart tissue-specific CK8e promoter.

Double VP64, C7 guide
(SEQ ID NO: 11)
cctggtatctttatagtcctgtcgggtttcgccacctctgacttgagcgtcgatttttgtgatgctcgtcaggggggcgg agcctatggaaaaacgccagcaacgcggcctttttacggttcctggccttttgctggccttttgctcacatgtcctgcag gcagctgcgcgctcgctcgctcactgaggccgcccgggcgtcgggcgacctttggtcgcccggcctcagtgagcgagcga gcgcgcagagagggagtggccaactccatcactaggggttcctgcggcctctagactcgagtgcccatgtaaggaggcaa ggcctggggacacccgagatgcctggttataattaacccagacatgtggctgcccccccccccccaacacctgctgcctc taaaaataaccctgcatgccatgttcccggcgaagggccagctgtcccccgccagctagactcagcacttagtttaggaa ccagtgagcaagtcagcccttggggcagcccatacaaggccatggggctgggcaagctgcacgcctgggtccggggtggg cacggtgcccgggcaacgagctgaaagctcatctgctctcaggggcccctccctggggacagcccctcctggctagtcac accctgtaggctcctctatataacccaggggcacaggggctgccctcattctaccaccacctccacagcacagacagaca ctcaggagccagccagcaccggtgccaccatgggtccgcgggctgacgcattggacgattttgatctggatatgctggga agtgacgccctcgatgattttgaccttgacatgcttggttcggatgcccttgatgactttgacctcgacatgctcggcag -continued tgacgcccttgatgatttcgacctggacatggttaacccaaagaagaagcggaaggtcggtatccacggagtcccagcag ccaagcggaactacatcctgggcctggccatcggcatcaccagcgtgggctacggcatcatcgactacgagacacgggac gtgatcgatgccggcgtgcggctgttcaaagaggccaacgtggaaaacaacgagggcaggcggagcaagagaggcgccag aaggctgaagcggcggaggcggcatagaatccagagagtgaagaagctgctgttcgactacaacctgctgaccgaccaca gcgagctgagcggcatcaacccctacgaggccagagtgaagggcctgagccagaagctgagcgaggaagagttctctgcc gccctgctgcacctggccaagagaagaggcgtgcacaacgtgaacgaggtggaagaggacaccggcaacgagctgtccac caaagagcagatcagccggaacagcaaggccctggaagagaaatacgtggccgaactgcagctggaacggctgaagaaag acggcgaagtgcggggcagcatcaacagattcaagaccagcgactacgtgaaagaagccaaacagctgctgaaggtgcag aaggcctaccaccagctggaccagagcttcatcgacacctacatcgacctgctggaaacccggcggacctactatgaggg acctggcgagggcagccccttcggctggaaggacatcaaagaatggtacgagatgctgatgggccactgcacctacttcc ccgaggaactgcggagcgtgaagtacgcctacaacgccgacctgtacaacgccctgaacgacctgaacaatctcgtgatc accagggacgagaacgagaagctggaatattacgagaagttccagatcatcgagaacgtgttcaagcagaagaagaagcc caccctgaagcagatcgccaaagaaatcctcgtgaacgaagaggatattaagggctacagagtgaccagcaccggcaagc ccgagttcaccaacctgaaggtgtaccacgacatcaaggacattaccgcccggaaagagattattgagaacgccgagctg ctggatcagattgccaagatcctgaccatctaccagagcagcgaggacatccaggaagaactgaccaatctgaactccga gctgacccaggaagagatcgagcagatctctaatctgaagggctataccggcacccacaacctgagcctgaaggccatca acctgatcctggacgagctgtggcacaccaacgacaaccagatcgctatcttcaaccggctgaagctggtgcccaagaag gtggacctgtcccagcagaaagagatccccaccaccctggtggacgacttcatcctgagccccgtcgtgaagagaagctt catccagagcatcaaagtgatcaacgccatcatcaagaagtacggcctgcccaacgacatcattatcgagctggcccgcg agaagaactccaaggacgcccagaaaatgatcaacgagatgcagaagcggaaccggcagaccaacgagcggatcgaggaa atcatccggaccaccggcaaagagaacgccaagtacctgatcgagaagatcaagctgcacgacatgcaggaaggcaagtg cctgtacagcctggaagccatccctctggaagatctgctgaacaaccccttcaactatgaggtggaccacatcatcccca gaagcgtgtccttcgacaacagcttcaacaacaaggtgctcgtgaagcaggaagaagccagcaagaagggcaaccggacc ccattccagtacctgagcagcagcgacagcaagatcagctacgaaaccttcaagaagcacatcctgaatctggccaaggg caagggcagaatcagcaagaccaagaaagagtatctgctggaagaacgggacatcaacaggttctccgtgcagaaagact tcatcaaccggaacctggtggataccagatacgccaccagaggcctgatgaacctgctgcggagctacttcagagtgaac aacctggacgtgaaagtgaagtccatcaatggcggcttcaccagctttctgcggcggaagtggaagtttaagaaagagcg gaacaaggggtacaagcaccacgccgaggacgccctgatcattgccaacgccgatttcatcttcaaagagtggaagaaac tggacaaggccaaaaaagtgatggaaaaccagatgttcgaggaaaagcaggccgagagcatgcccgagatcgaaaccgag caggagtacaaagagatcttcatcaccccccaccagatcaagcacattaaggacttcaaggactacaagtacagccaccg ggtggacaagaagcctaatagagagctgattaacgacaccctgtactccacccggaaggacgacaagggcaacaccctga tcgtgaacaatctgaacggcctgtacgacaaggacaatgacaagctgaaaaagctgatcaacaagagccccgaaaagctg ctgatgtaccaccacgacccccagacctaccagaaactgaagctgattatggaacagtacggcgacgagaagaatcccct gtacaagtactacgaggaaaccgggaactacctgaccaagtactccaaaaaggacaacggccccgtgatcaagaagatta agtattacggcaacaaactgaacgcccatctggacatcaccgacgactaccccaacagcagaaacaaggtcgtgaagctg tccctgaagccctacagattcgacgtgtacctggacaatggcgtgtacaagttcgtgaccgtgaagaatctggatgtgat caaaaaagaaaactactacgaagtgaatagcaagtgctatgaggaagctaagaagctgaagaagatcagcaaccaggccg agtttatcgcctccttctacaacaacgatctgatcaagatcaacggcgagctgtatagagtgatcggcgtgaacaacgac ctgctgaaccggatcgaagtgaacatgatcgacatcacctaccgcgagtacctggaaaacatgaacgacaagaggccccc caggatcattaagacaatcgcctccaagacccagagcattaagaagtacagcacagacattctgggcaacctgtatgaag -continued tgaaatctaagaagcaccctcagatcatcaaaaagggcaaaaggccggcggccacgaaaaaggccggccaggcaaaaaag aaaaagggatccgacgcgctggacgatttcgatctcgacatgctgggttctgatgccctcgatgactttgacctggatat gttgggaagcgacgcattggatgactttgatctggacatgctcggctccgatgctctggacgatttcgatctcgatatgt tataagaattcatcgataccgtcgagatctaacttgtttattgcagcttataatggttacaaataaagcaatagcatcac aaatttcacaaataaagcatttttttcactgcattctagttgtggtttgtccaaactcatcaatgtatcttatcatgtct ggaggtaccgagggcctatttcccatgattccttcatatttgcatatacgatacaaggctgttagagagataattggaat taatttgactgtaaacacaaagatattagtacaaaatacgtgacgtagaaagtaataatttcttgggtagtttgcagttt taaaattatgttttaaaatggactatcatatgcttaccgtaacttgaaagtatttcgatttcttggctttatatatcttg tggaaaggacgaaacaccgATCATGCGAAAGGGGAGCTGTgttttagtactctggaaacagaatctactaaa acaaggcaaaatgccgtgtttatctcgtcaacttgttggcgagatttttgcggccgcaggaacccctagtgatggagttggccact ccctctctgcgcgctcgctcgctcactgaggccgggcgaccaaaggtcgcccgacgcccgggctttgcccgggcggcctcag tgagcgagcgagcgcgcagctgcctgcaggggcgcctgatgcggtattttctccttacgcatctgtgcggtatttcacac cgcatacgtcaaagcaaccatagtacgcgccctgtagcggcgcattaagcgcggcgggtgtggtggttacgcgcagcgtg accgctacacttgccagcgccttagcgcccgctcctttcgctttcttcccttcctttctcgccacgttcgccggctttcc ccgtcaagctctaaatcgggggctccctttagggttccgatttagtgctttacggcacctcgaccccaaaaaacttgatt tgggtgatggttcacgtagtgggccatcgccctgatagacggtttttcgccctttgacgttggagtccacgttctttaat agtggactcttgttccaaactggaacaacactcaactctatctcgggctattcttttgatttataagggattttgccgat ttcggtctattggttaaaaaatgagctgatttaacaaaaatttaacgcgaattttaacaaaatattaacgtttacaattt tatggtgcactctcagtacaatctgctctgatgccgcatagttaagccagccccgacacccgccaacacccgctgacgcg ccctgacgggcttgtctgctcccggcatccgcttacagacaagctgtgaccgtctccgggagctgcatgtgtcagaggtt ttcaccgtcatcaccgaaacgcgcgagacgaaagggcctcgtgatacgcctatttttataggttaatgtcatgataataa tggtttcttagacgtcaggtggcacttttcggggaaatgtgcgcggaacccctatttgtttatttttctaaatacattca aatatgtatccgctcatgagacaataaccctgataaatgcttcaataatattgaaaaaggaagagtatgagtattcaaca tttccgtgtcgcccttattcccttttttgcggcattttgccttcctgtttttgctcacccagaaacgctggtgaaagtaa aagatgctgaagatcagttgggtgcacgagtgggttacatcgaactggatctcaacagcggtaagatccttgagagtttt cgccccgaagaacgttttccaatgatgagcacttttaaagttctgctatgtggcgcggtattatcccgtattgacgccgg gcaagagcaactcggtcgccgcatacactattctcagaatgacttggttgagtactcaccagtcacagaaaagcatctta cggatggcatgacagtaagagaattatgcagtgctgccataaccatgagtgataacactgcggccaacttacttctgaca acgatcggaggaccgaaggagctaaccgcttttttgcacaacatgggggatcatgtaactcgccttgatcgttgggaacc ggagctgaatgaagccataccaaacgacgagcgtgacaccacgatgcctgtagcaatggcaacaacgttgcgcaaactat taactggcgaactacttactctagcttcccggcaacaattaatagactggatggaggcggataaagttgcaggaccactt ctgcgctcggcccttccggctggctggtttattgctgataaatctggagccggtgagcgtggaagccgcggtatcattgc agcactggggccagatggtaagccctcccgtatcgtagttatctacacgacggggagtcaggcaactatggatgaacgaa atagacagatcgctgagataggtgcctcactgattaagcattggtaactgtcagaccaagtttactcatatatactttag attgatttaaaacttcatttttaatttaaaaggatctaggtgaagatcctttttgataatctcatgaccaaaatccctta acgtgagttttcgttccactgagcgtcagaccccgtagaaaagatcaaaggatcttcttgagatcctttttttctgcgcg taatctgctgcttgcaaacaaaaaaaccaccgctaccagcggtggtttgtttgccggatcaagagctaccaactctttttt ccgaaggtaactggcttcagcagagcgcagataccaaatactgttcttctagtgtagccgtagttaggccaccacttcaa gaactctgtagcaccgcctacatacctcgctctgctaatcctgttaccagtggctgctgccagtggcgataagtcgtgtc -continued ttaccgggttggactcaagacgatagttaccggataaggcgcagcggtcgggctgaacggggggttcgtgcacacagccc agcttggagcgaacgacctacaccgaactgagatacctacagcgtgagctatgagaaagcgccacgcttcccgaagggagaa aggcggacaggtatccggtaagcggcagggtcggaacaggagagcgcacgagggagcttccagggggaaacg The results of the experiments are now described.

Example 1: Upregulating Alternate Isoforms of Dystrophin to Compensate for the Absence of Muscle Dystrophin in Duchenne Muscular Dystrophy (DMD)

A patient was diagnosed with DMD due to a deletion of the promoter and exon 1 in their dystrophin gene (muscle isoform). Experiments were designed to restore full length expression of dystrophin by upregulating alternate brain isoforms of dystrophin (purkinje or cortical). The purkinje (Dp427p) and cortical (Dp427c) isoforms of dystrophin both encode a full-length protein of 79 exons, differing only in exon 1 to muscle dystrophin. Herein, these alternate dystrophin isoforms, purkinje and cortical isoforms, were upregulated using a CRISPR activation system.

Figure 2A:
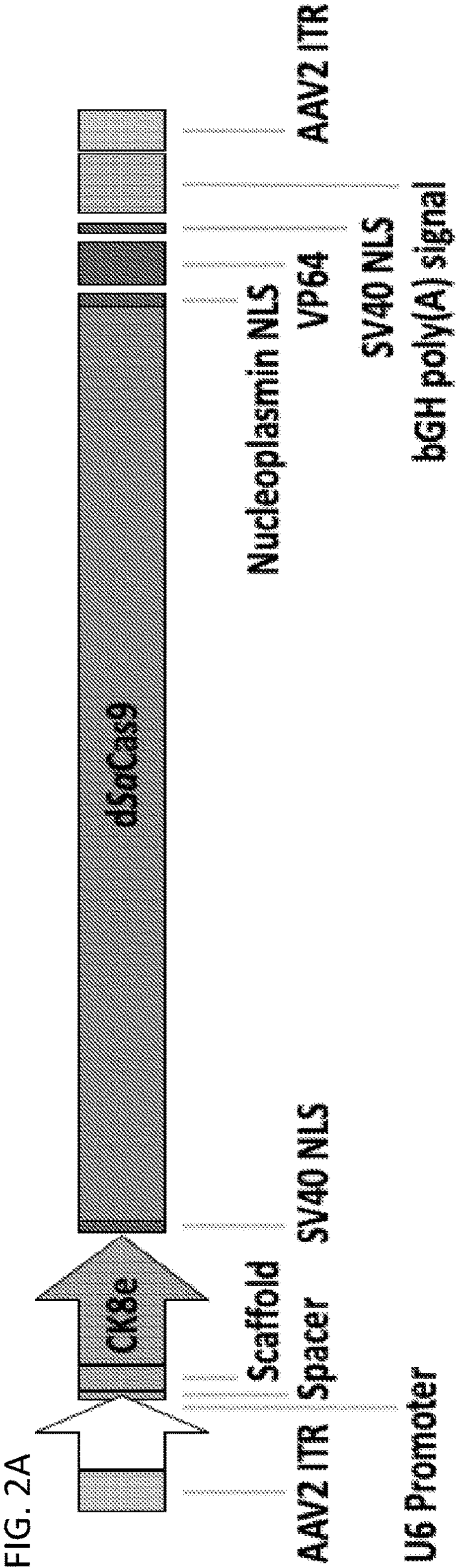
FIGS. 2A-2B: AAV plasmid design for in vitro and in vivo delivery of CRISPR activation machinery, based on the concept depicted in FIGS. 1A and 1B, to achieve upregulation of alternate dystrophin isoforms.
Figure 2B:
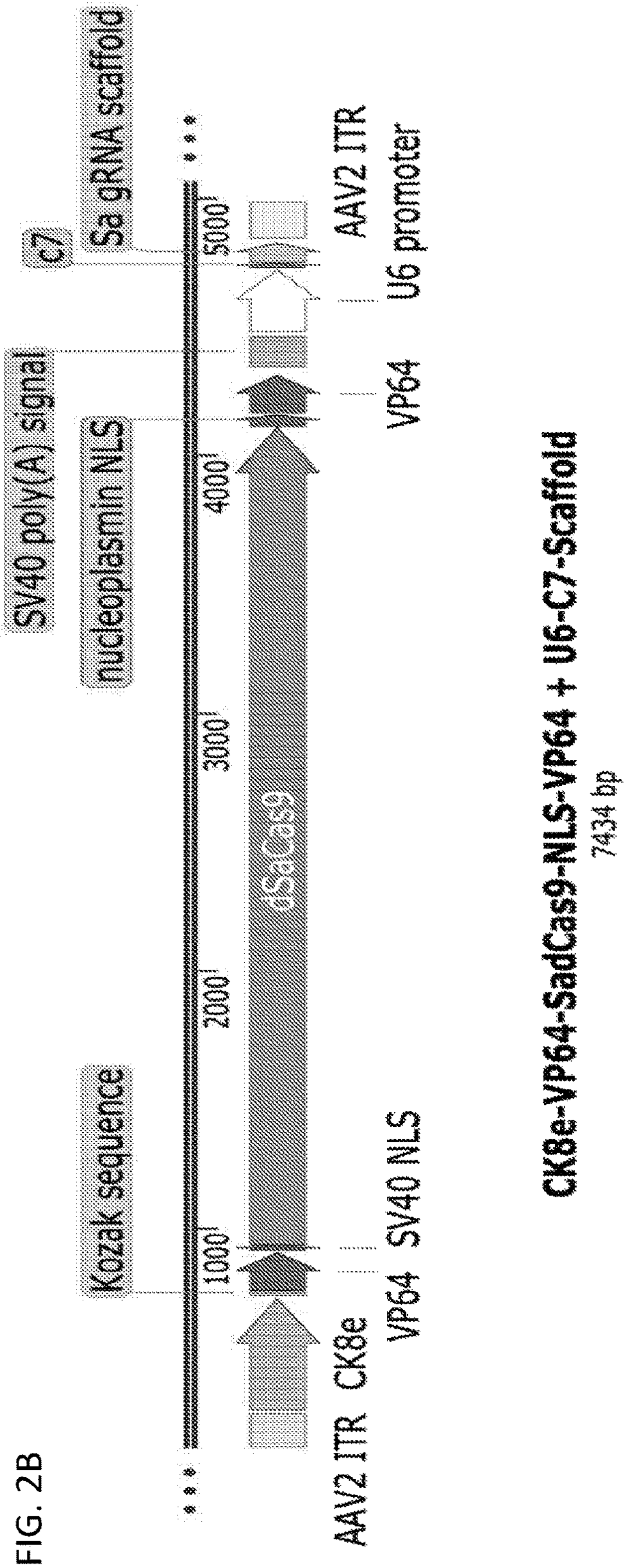

Guide RNAs were designed to target the promoter region of the alternate dystrophin isoforms (purkinje and cortical) in order to direct the CRISPR-dCas9-VP64 activation machinery to these brain isoforms and upregulate their expression in the absence of the muscle isoform of dystrophin (FIG. 1). AAV plasmids from Addgene® were modified for in vitro and in vivo delivery of the CRISPR activation machinery to achieve upregulation of the alternate dystrophin isoforms (FIG. 2). A single and double VP64 plasmid design was adopted from Addgene® plasmid #99680 (single) and plasmid #135338 (double). In both instances, the CMV promoter was exchanged for a muscle-specific CK8e promoter.

Figure 3:
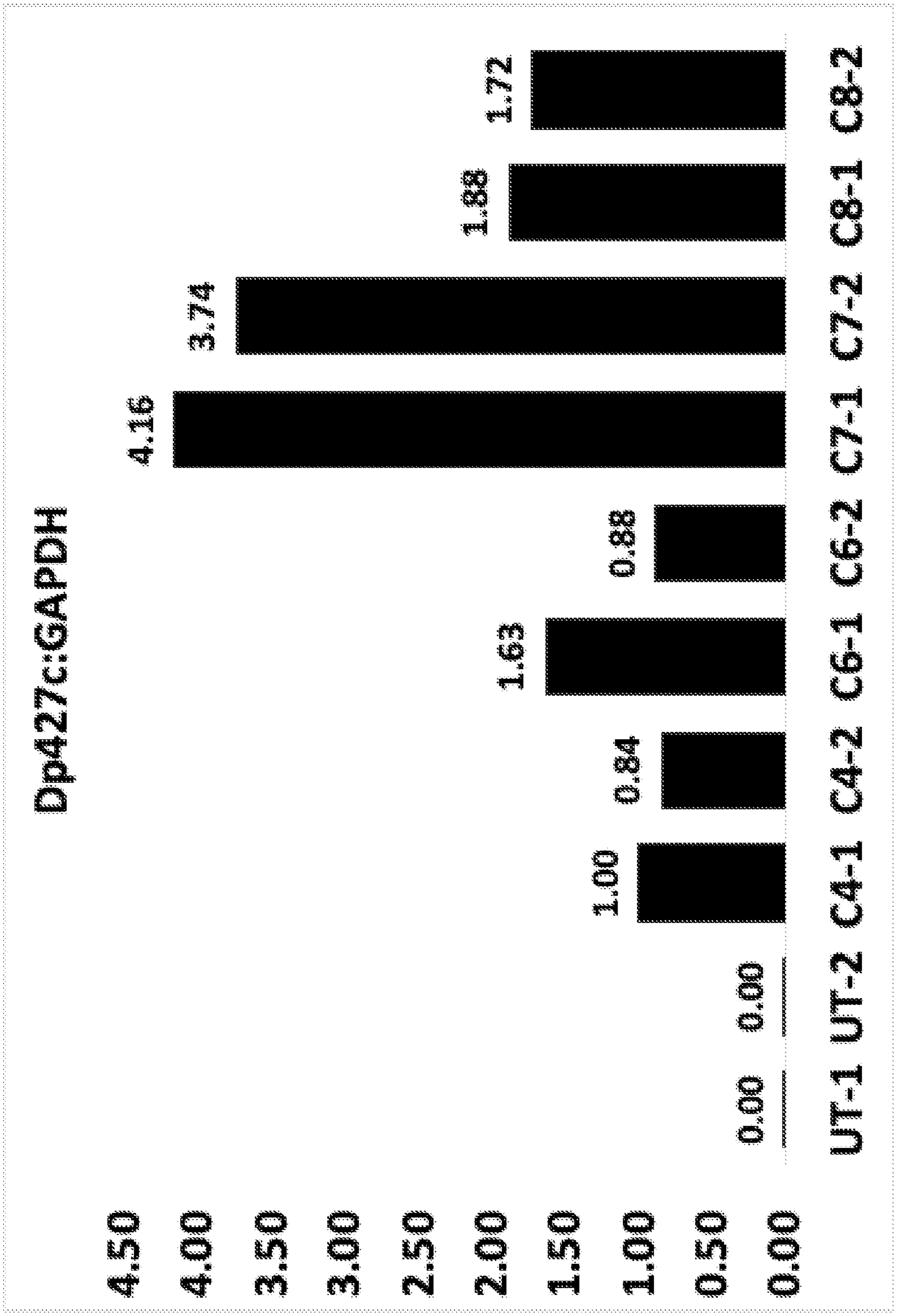
FIG. 3: Quantitative PCR results of the single VP64 plasmid (FIG. 2A) with guides C4 (SEQ ID NO: 4), C6 (SEQ ID NO: 5), C7 (SEQ ID NO: 6) and C8 (SEQ ID NO: 7) cloned in showing varying levels of cortical dystrophin upregulation.
Figure 4A:
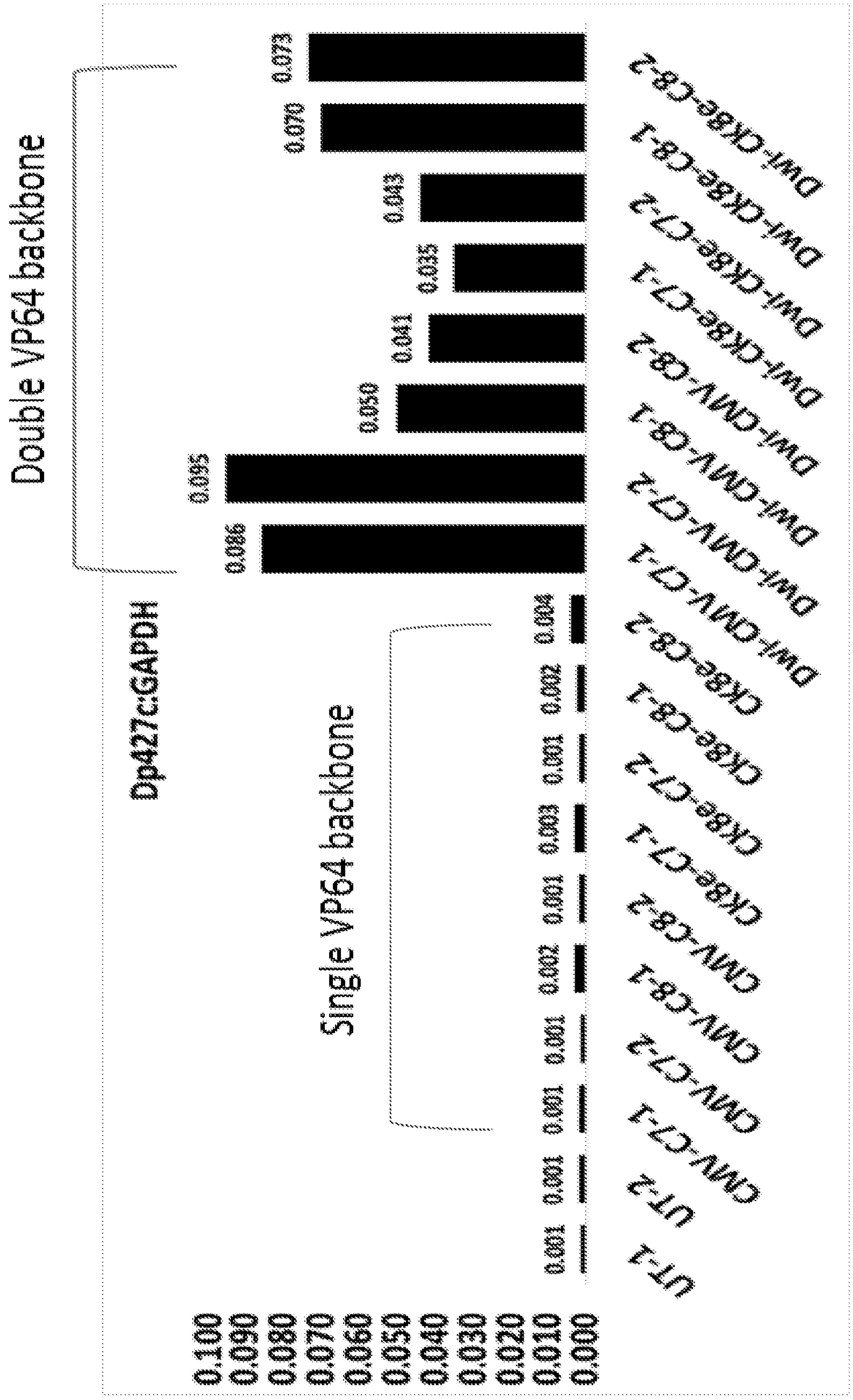
FIGS. 4A-4B: qPCR (FIG. 4A) and RT-PCR (FIG. 4B) results showing upregulation of cortical dystrophin (Dp427c) in cells using C7 and C8 guides cloned into AAV plasmids with a single VP64 and double transactivator (FIGS. 2A and 2B).
Figure 4B:
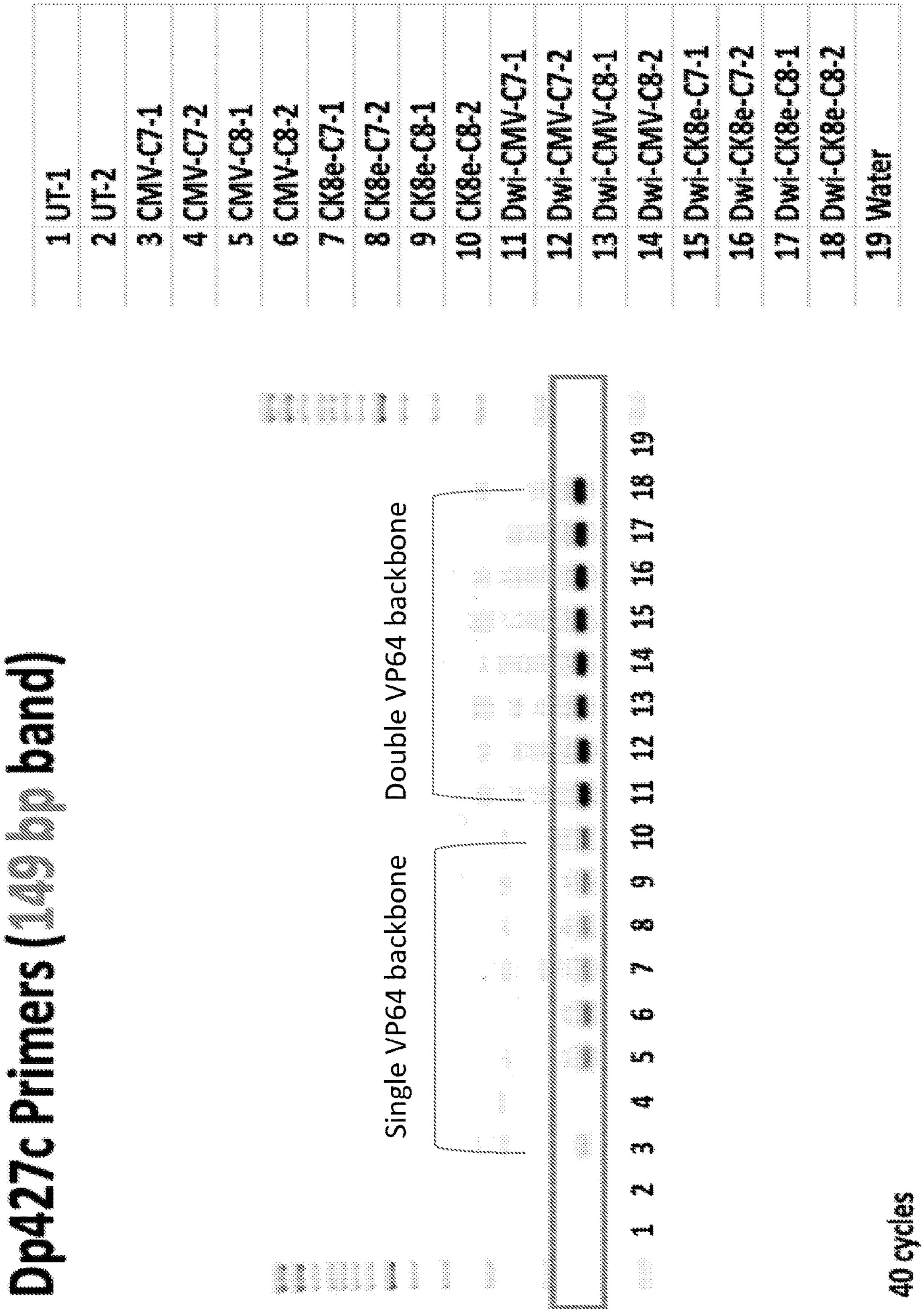

For the single VP64 plasmid, components from Addgene® plasmid #99690 (U6 promoter and guide RNA scaffold) were also inserted. Four different guide sequences (SEQ ID NOs: 4-7) were tested and successfully upregulated cortical dystrophin transcripts at varying levels in cells (FIG. 3). Quantitative PCR and RT-PCR results showed successful upregulation of cortical dystrophin transcripts using the single and double VP64 CRISPR-activation machinery with C7 (SEQ ID NO: 6) and C8 (SEQ ID NO: 7) guides (FIGS. 4A and 4B).

Example 2: In Vivo Delivery of AAV

In vivo delivery of AAV constructs is tested using a humanized DMD mouse model bred into a D2-mdx background (missing mouse dystrophin) to assess upregulation of alternate isoforms in skeletal and cardiac muscles.

This model tests systemic delivery of AAV constructs for safety, efficacy and dosing. The following end-points are assessed: 1) Upregulation of global levels of dystrophin in skeletal and cardiac muscles (above untreated levels). Tissues are harvested for both IHC and western blot analysis using a dystrophin antibody. In cases where these techniques are sensitive enough to detect upregulation above that of endogenous dystrophin levels, alternative methods are used. 2) Skeletal and cardiac muscles are harvested and assessed for Cas9 expression via IHC to determine the extent of delivery and uptake of the AAV construct. 3) Skeletal and cardiac muscles are harvested for RNA isolation to quantify dystrophin upregulation on a transcript level by qPCR. Primers are designed to specifically detect cortical and purkinje isoforms in a qPCR reaction to delineate from muscle isoform of dystrophin expressed at baseline in this model.

An exon 1 knock-out mutation is introduced into the humanized DMD line to generate a dystrophin-null model (which still harbors the genetic elements to upregulate the alternate dystrophin isoforms). This line results in a quantifiable muscle pathology on both a structural and functional level and is used to assess efficacy of dystrophin restoration via the therapeutic strategy disclosed herein. Using this exon 1 knock-out model, the optimal AAV dose, as determined above, is delivered.

Muscle tissue is harvested from treated and control group mice and assessed for: 1) Restoration of dystrophin protein expression by western blot and IHC, as well as restoration of the components at the sarcolemma e.g. DGC complex. 2) Improvement in muscle structure: H&E staining, Evans blue dye uptake and/or IgG staining, laminin staining. 3) Improvement in muscle function: treadmill running, ex vivo EDL force and fatigue.

Presented herein is a novel CRISPR-based therapeutic strategy for DMD. Current CRISPR-based therapy for DMD involves exon-skipping approaches for a specific mutation class. The utility of a CRISPR-based gene upregulation strategy has not been tried for isoforms of dystrophin. Results were demonstrated in patient cells and a single AAV construct was designed for in vivo delivery. The invention provides a personalized genetic therapy for a DMD patient, i.e. for a patient who may not a candidate for therapies in clinical trials due to an uncommon mutation in the DMD gene. This approach can result in expression of full-length dystrophin or isoforms larger than mini-dystrophin, albeit using a different promoter and exon 1, so is presumed to impart more functional restoration to patients than mini-dystrophin gene therapy.

Figure 5:
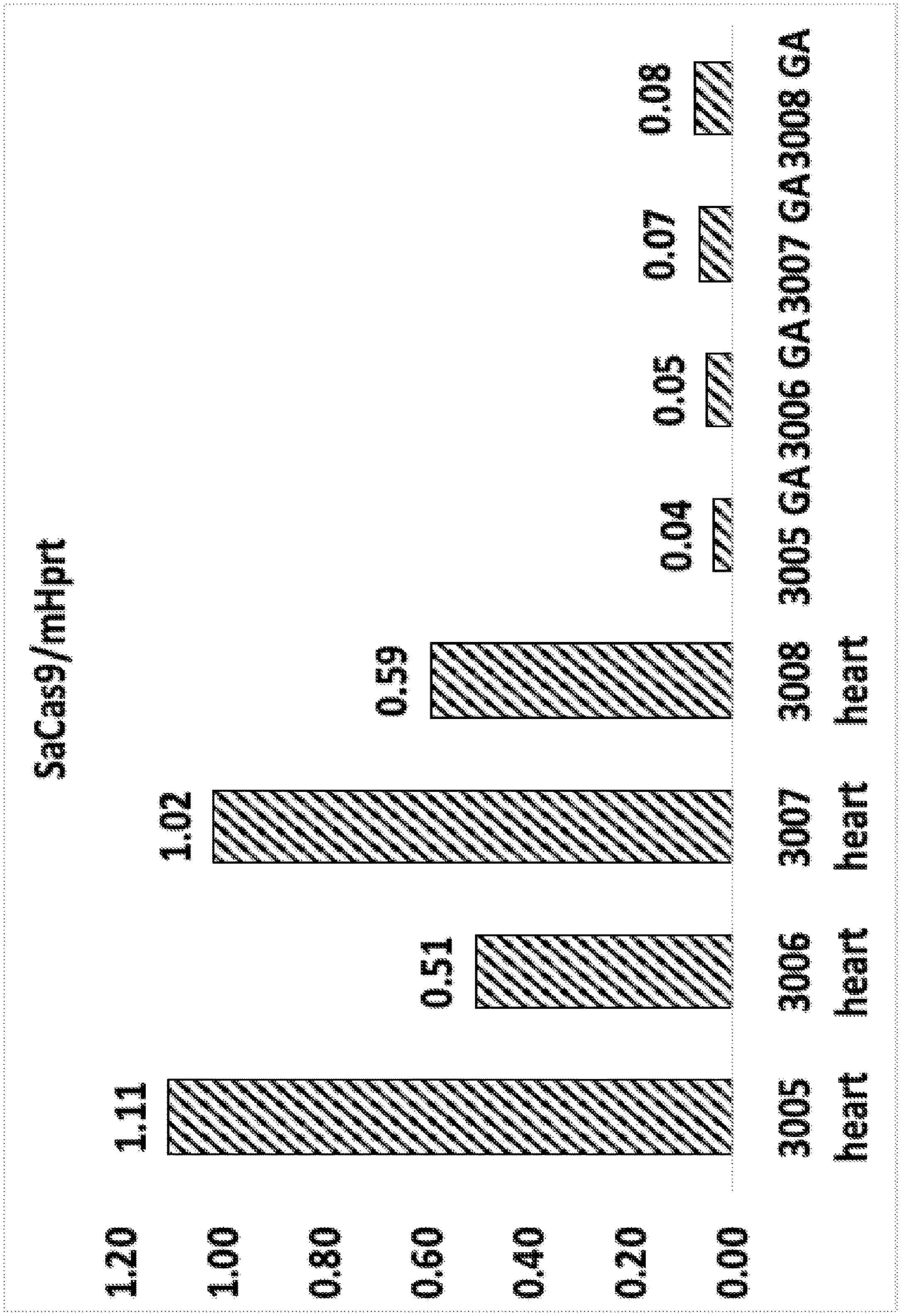
FIG. 5: SaCas9 RNA expression validated in high-dose mouse hearts at 8 weeks post-treatment.
Figure 6:
FIG. 6: SaCas9 protein expression validated in high-dose mouse hearts at 4- and 8-week time points.
Figure 7:
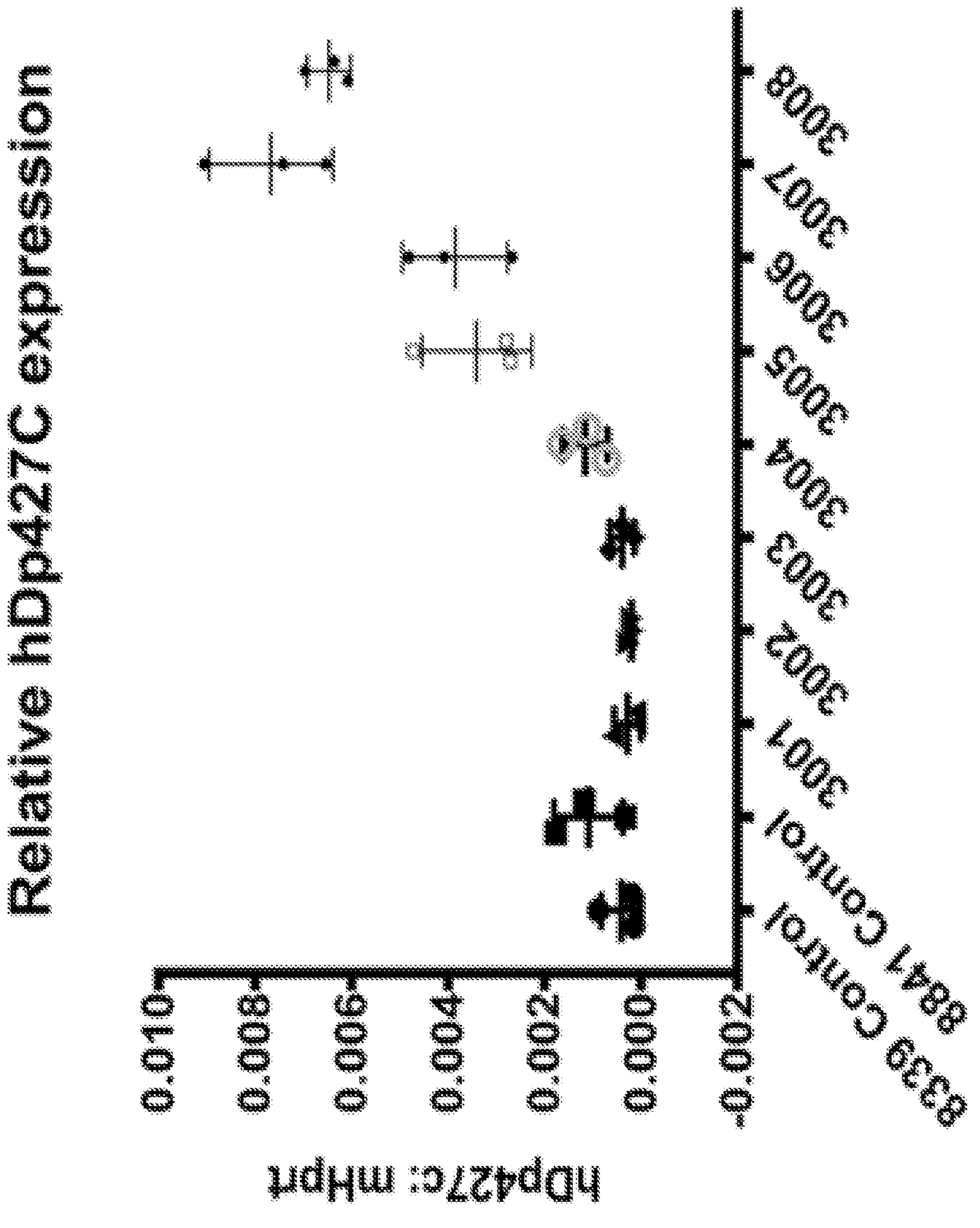
FIG. 7: Dp427c RNA up-regulation observed in high dose 4-week hearts by qPCR quantification. Low dose heart: lanes 3001-3004; High dose heart: 3005-3008.

Example 3: Pre-Clinical Data Demonstrates Systemic Dystrophin Cortical Isoform Up-Regulation in Mice The CRISPRa single VP64 construct with the C7 guide was packaged into AAV9 for systemic delivery in hDMD-D2 mice via tail vein injection at low ($2.8\times10^{13}$) and high ($2.8\times10^{14}$) doses. Mice were sacrificed at 4 and 8-weeks post injection with tissues harvested and preserved for RNA and protein analysis. Heart tissue demonstrated abundance of SaCas9 transcripts, with lower levels detected in gastrocnemius muscle (FIG. 5). SaCas9 protein was also detected in heart tissue from 4- and 8-week treated high-dose cohorts (FIG. 6). Cortical dystrophin (Dp427c) transcript levels were increased above untreated mice as determined via quantitative PCR (FIG. 7). Similar in vivo experiments are performed with the CRISPRa double VP64 construct with the C7 guide.

ENUMERATED EMBODIMENTS

The following enumerated embodiments are provided, the numbering of which is not to be construed as designating levels of importance.

Embodiment 1 provides a method of treating a disease or disorder in a subject in need thereof, wherein the disease or disorder is associated with aberrant or absent dystrophin, the method comprising administering to the subject a composition that upregulates a brain isoform of dystrophin.

Embodiment 2 provides the method of embodiment 1, wherein the brain isoform of dystrophin is selected from the group consisting of purkinje and cortical.

Embodiment 3 provides the method of embodiment 1, wherein the disease is Duchenne Muscular Dystrophy (DMD).

Embodiment 4 provides the method of embodiment 1, wherein the disease is X-linked cardiomyopathy.

Embodiment 5 provides the method of embodiment 1, wherein the subject has an absence of muscle dystrophin.

Embodiment 6 provides the method of embodiment 1, wherein the subject has a mutation or deletion in the promoter and/or exon 1 of the muscle dystrophin gene.

Embodiment 7 provides the method of embodiment 1, wherein the composition comprises a CRISPR activation (CRISPRa) system that upregulates the brain isoform of dystrophin.

Embodiment 8 provides the method of embodiment 7, wherein the CRISPRa system comprises an AAV vector comprising a tissue-specific promoter.

Embodiment 9 provides the method of embodiment 7, wherein the CRISPRa system comprises an AAV vector comprising a muscle-specific promoter.

Embodiment 10. provides the method of embodiment 7 or embodiment 8, wherein the promoter yields expression of the vector in skeletal muscle tissue and/or cardiac tissue.

Embodiment 11 provides the method of embodiment 8, wherein the promoter is a muscle creatine kinase 8 (CK8e) promoter.

Embodiment 12 provides the method of embodiment 7, wherein the CRISPRa system comprises a guide RNA that targets the cortical dystrophin promoter region.

Embodiment 13 provides the method of embodiment 12, wherein the gRNA target region comprises a nucleotide sequence selected from the group consisting of SEQ ID NO: 4-7.

Embodiment 14 provides the method of embodiment 7, wherein the CRISPRa system comprises a guide RNA that targets the purkinje dystrophin promoter region.

Embodiment 15 provides the method of embodiment 12, wherein the gRNA target region comprises a nucleotide sequence selected from the group consisting of SEQ ID NO: 8-10.

Embodiment 16 provides the method of embodiment 8, wherein the AAV vector comprises the nucleotide sequence of SEQ ID NO: 11.

Embodiment 17 provides the method of embodiment 7, wherein the CRISPR activation (CRISPRa) system is a single vector system.

Embodiment 18 provides a pharmaceutical composition comprising an AAV vector comprising an MHCK7 promoter and a gRNA sequence that targets the cortical dystrophin promoter region or the purkinje dystrophin promoter region.

Embodiment 19 provides a pharmaceutical composition comprising an AAV vector comprising a CK8e promoter and a gRNA sequence that targets the cortical dystrophin promoter region or the purkinje dystrophin promoter region.

Embodiment 20 provides the pharmaceutical composition of embodiment 19, wherein the AAV vector comprises the nucleotide sequence set forth in SEQ ID NO: 11.

Embodiment 21 provides the pharmaceutical composition of embodiment 19, wherein the gRNA sequence comprises a nucleotide sequence selected from the group consisting of SEQ ID NO: 4-10.

OTHER EMBODIMENTS

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating a disease or disorder in a subject in need thereof, wherein the disease or disorder is associated with aberrant or absent dystrophin, the method comprising administering to the subject a composition that upregulates a cortical isoform of dystrophin, wherein the disease is Duchenne Muscular Dystrophy (DMD), wherein the composition comprises a CRISPR activation (CRISPRa) system that upregulates the cortical isoform of dystrophin, wherein the CRISPRa system comprises a guide RNA (gRNA) that targets the cortical dystrophin promoter region or the Purkinje dystrophin promoter region, and wherein the CRISPRa system comprises an AAV vector comprising the nucleotide sequence of SEQ ID NO: 11.

2. The method of claim 1, wherein the subject has an absence of muscle dystrophin.

3. The method of claim 1, wherein the subject has a mutation or deletion in the promoter and/or exon 1 of the muscle dystrophin gene.

4. The method of claim 1, wherein the CRISPR activation (CRISPRa) system is a single vector system.

5. A pharmaceutical composition comprising an AAV vector comprising a CK8e promoter and a guide RNA (gRNA) sequence that targets the cortical dystrophin promoter region, wherein the AAV vector comprises the nucleotide sequence set forth in SEQ ID NO: 11.

* * * * *